US008288422B2

(12) United States Patent
Loso et al.

(10) Patent No.: US 8,288,422 B2
(45) Date of Patent: *Oct. 16, 2012

(54) INSECTICIDAL N-SUBSTITUTED (6-HALOOALKYLPYRIDIN-3-YL)-ALKYL SULFOXIMINES

(75) Inventors: Michael R. Loso, Carmel, IN (US); Benjamin M. Nugent, Brownsburg, IN (US); Jim X. Huang, Carmel, IN (US); Richard B. Rogers, Mobile, AL (US); Yuanming Zhu, Carmel, IN (US); James M. Renga, Indianapolis, IN (US); Vidyadhar B. Hegde, Carmel, IN (US); Joseph J. DeMark, Fayetteville, AP (US)

(73) Assignee: Dow AgroSciences, LLC., Indianapolis, IN (US)

( * ) Notice: Subject to any disclaimer, the term of this patent is extended or adjusted under 35 U.S.C. 154(b) by 147 days.

This patent is subject to a terminal disclaimer.

(21) Appl. No.: 12/706,552

(22) Filed: Feb. 16, 2010

(65) Prior Publication Data

US 2010/0179099 A1  Jul. 15, 2010

Related U.S. Application Data

(63) Continuation-in-part of application No. 11/704,842, filed on Feb. 9, 2007, now Pat. No. 7,687,634.

(60) Provisional application No. 60/772,108, filed on Feb. 10, 2006, provisional application No. 60/836,044, filed on Aug. 7, 2006.

(51) Int. Cl.
A01N 43/40 (2006.01)
(52) U.S. Cl. ..................... 514/357
(58) Field of Classification Search ............. 514/357
See application file for complete search history.

(56) References Cited

U.S. PATENT DOCUMENTS

| 3,711,486 A | 1/1973 | Torba et al. |
| 3,787,420 A | 1/1974 | Torba et al. |
| 3,852,279 A | 12/1974 | Krapcho et al. |
| 4,577,028 A | 3/1986 | Martin et al. |
| 4,692,184 A | 9/1987 | Lee |
| 4,747,871 A | 5/1988 | Ruminski et al. |
| 4,833,158 A | 5/1989 | Twydell et al. |
| 4,948,896 A | 8/1990 | Nagao |
| 4,973,695 A | 11/1990 | Yamashita et al. |
| 5,053,516 A | 10/1991 | Hartmann et al. |
| 5,099,023 A | 3/1992 | Miller et al. |
| 5,099,024 A | 3/1992 | Pulwer et al. |
| 5,118,809 A | 6/1992 | Cevasco et al. |
| 5,124,458 A | 6/1992 | Cevasco et al. |
| 5,169,432 A | 12/1992 | Auinbauh et al. |
| 5,225,560 A | 7/1993 | Cevasco et al. |
| 5,227,491 A | 7/1993 | Doehner, Jr. |
| 5,229,519 A | 7/1993 | Zhang et al. |
| 6,060,502 A | 5/2000 | Lowder et al. |
| 7,511,149 B2 | 3/2009 | Arndt et al. |
| 7,541,469 B2 | 6/2009 | Renga et al. |
| 7,604,815 B2 | 10/2009 | Loso et al. |
| 7,678,920 B2 | 3/2010 | Zhu et al. |
| 2003/0078430 A1 | 4/2003 | Satake et al. |
| 2004/0158067 A1 | 8/2004 | Hutchison et al. |
| 2006/0199964 A1 | 9/2006 | Jackson et al. |
| 2007/0203191 A1 | 8/2007 | Loso et al. |
| 2007/0249837 A1 | 10/2007 | Gebhardt et al. |
| 2007/0299264 A1 | 12/2007 | Huang et al. |
| 2008/0108665 A1 | 5/2008 | Huang et al. |
| 2008/0108666 A1 | 5/2008 | Loso et al. |
| 2008/0108667 A1 | 5/2008 | Zhu et al. |
| 2008/0132705 A1 | 6/2008 | Heller et al. |
| 2008/0194830 A1 | 8/2008 | Meyer et al. |
| 2008/0280915 A1 | 11/2008 | Loso et al. |
| 2010/0152245 A1* | 6/2010 | Loso et al. ............... 514/336 |
| 2010/0168172 A1* | 7/2010 | Loso et al. ............... 514/332 |
| 2010/0168177 A1* | 7/2010 | Qin et al. ............... 514/336 |
| 2010/0168178 A1* | 7/2010 | Qin et al. ............... 514/336 |

FOREIGN PATENT DOCUMENTS

| DE | 19523658 | 6/1995 |
| WO | W098/02492 | 1/1998 |
| WO | WO01/07430 | 2/2001 |

OTHER PUBLICATIONS

Kagabu, Shinzo and Medej, Somporn; "Stability Comparison of Imidacloprid and Related Compounds under Simulated Sunlight, Hydrolysis Conditions, and to Oxygen;" Biosci. Biotech. Biochem., 59 (6), 980-985, (1995).

Kagabu, Shinzo; Murata, Natsue; Hibino, Rika; Hanzawa, Madoka and Nishimura, Keiichiro; "Insecticidal and Neuroblocking Activities of Thiamethoxam-Type Compounds in the American Cockroach (*Periplaneta americana* L.);" J. Pesticide Sci. 30(2), 111-115 (2005).

Sparks, Thomas C.; Crouse, Gary D. and Durst, Gregory; "Natural products as insecticides: the biology, biochemistry and quantitative structure-activity relationships of spinosyns and spinosoids;" Pest Management Science, 57:896-905 (2001).

Wakita, Takeo; Kinoshita, Katsutoshi; Kodaka, Kenji; Yasui, Naoko; Naoi, Atsuko and Banba, Sinichi; "Synthesis and Structure-Activity Relationships of Dinotefuran Derivatives: Modification in the Tetrahydro-3-furylmethyl Part;" J. Pesticide Sci. 29 (4), 356-363 (2004).

Kollmeyer, Willy D.; Flattum, Roger F.; Foster, James P.; Powell, James E.; Schroeder, Mark E. and Soloway, S. Barney; "Discovery of the Nitromethylene Heterocycle Insecticides;" Nicotinoid Insecticides and the Nicotinic Acetylcholine Receptor [Eds.: Yamamoto, I. and Casida, J.E.]; 1999, pp. 71-89, Springer-Verlag, Tokyo.

Shiga, Yasushi; Okada, Itaru and Fukuchi, Toshiki; "Synthesis and Acaricidal Activity of N-(1,3,4-Thiadiazol-2-yl)cyclopropanecarboxamides;" J. Pesticide Sci. 28, 61-63 (2003).

(Continued)

Primary Examiner — Janet Andres
Assistant Examiner — John Mabry
(74) Attorney, Agent, or Firm — Carl D. Corvin; Craig E. Mixan

(57) ABSTRACT

N-Substituted (6-haloalkylpyridin-3-yl)alkyl sulfoximines are effective at controlling insects.

44 Claims, No Drawings

OTHER PUBLICATIONS

Singer, Alvin; McElvain, S.M. 2,6-Dimethylpyridine. Organic Syntheses, 1934, 14, 30.

Haibo Yu, Zhenfang Qin, Hong Dai, Xin Zhang, Xue Qin, Tingting Wang and Jianxin Fang, Synthesis and Insecticidal Activity of N-Substituted (1,3-Thiazole)alkyl Sulfoximine Derivatives, J. Agric. Food Chem. 2008, 56, 11356-11360.

Haibo Yu, Zhenfang Qin, Hong Dai, Xin Zhang, Xue Qin, Tingting Wang, and Jianxin Fang, Synthesis and insecticidal activity of N-cyano 2-(substituted amino) ethyl methyl sulfoximine derivatives, General Papers, ARKIVOC 2008 (xvi) 99-109.

Kawanshi, Hiroyuki; Morimoto, Hiroshi; Nakano, Takao; Watanabe, Tatsuya; Oda, Kuniyuki; and Tsujihara, Kenji; "Steroselective Synthesis of Antifungal Sulfoximines, Novel Trizaoles II;" Heterocycles, vol. 49, 1998, pp. 181-189.

Reichert, Anja; Frohlich, Roland; Ferguson, Roderick; Kraft, Arno; "Binding Interactions Between 3-aryl-1,2,4-oxadiazol-5-ones and a trisimidazoline base;" J. Chem. Soc., Perkin Trans. 1, 2001, pp. 1321-1328.

Garcia Mancheno, Olga; Bistri, Olivia; and Bolm, Carsten; "Iodinane- and Metal-Free Synthesis of N-Cyano Sulfilimines: Novel and Easy Access of NH-Sulfoximines;" Organic Letters, 2007, vol. 9, No. 19, pp. 3809-3811.

Kiriyama K et al: Insecticidal and neuroblocking activities of acetamiprid and related compounds Journal of Pesticide Sciences, Pesticide Science Society, Tokyo, JP, vol. 28, No. 1, 2003, pp. 80-17.

F Zaragoza Dorwald Side Reactions in Organic Synthesis 2005, Wiley-VCH.

Ortho Lithiation of S-ter-butyl-S-phenylsulfoximines (Tetrahedron), Stephane Gaillard, Mar. 29, 2005.

Yoshide et al: "The Cycloaddition Reaction of N-Imidoyl Sulfoximides with Diphenylcyclopropenone to Yield Pyrimidinone or Pyrrolinone Derivatives" The Chemical Society of Japan, Sep. 29, 1982.

Veale et al: "New Method in Preparation of Acyl- and Sulfonysulfoximines Ruthenium Tetroxide Oxidation of Sulfilmines" Tetrahedron Letters, No. 6, pp. 503-506, 1978.

Whittle et al: "Rearrangement Process in the Mass Spectra of N-Substituted Sulphoximines" Organic Mass Spectrometry, 1974, vol. 9, pp. 422-434.

Huang et al: "Oxidation of N-Acyl-, and N-Arylsulfilimines to Sulfoximines by m-Chloroperoxybenzoate Anion" J Org Chem, vol. 44 No. 14, 1979.

Garapon et al: "No 500—Reactions d'elminiations sur les o-chlorobenzoates d/anilide-oximes: formation des aryliminonitrenes sous l'action des bases azotees" Instiut Francois de Pelrole, B P 85, 38041, 1975.

Williams, Trevor et al., Biocontrol Science and Technology, "Is the Naturally Derived Insecticide Spinosad Compatible with Insect Natural Enemies", Aug. 2003, vol. 13, No. 15, pp. 459-475.

* cited by examiner

INSECTICIDAL N-SUBSTITUTED (6-HALOOALKYLPYRIDIN-3-YL)-ALKYL SULFOXIMINES

This application claims the benefit of U.S. Provisional Applications Ser. Nos. 60/772,108 filed on 10 Feb. 2006 and 60/836,044 filed on 7 Aug. 2006 and U.S. patent application Ser. No. 11/704,842 filed on 9 Feb. 2007, now allowed, the entire disclosures of which are all hereby incorporated by reference.

BACKGROUND OF THE INVENTION

The present invention concerns novel N-substituted (6-haloalkylpyridin-3-yl)alkyl sulfoximines and their use in controlling insects and certain other invertebrates, particularly aphids and other sucking insects. This invention also includes new synthetic procedures for preparing the compounds, pesticide compositions containing the compounds, and methods of controlling insects using the compounds.

There is an acute need for new insecticides. Insects are developing resistance to the insecticides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides. Therefore a need exists for new insecticides, and particularly for compounds that have new or atypical modes of action.

U.S. Patent Application Publication 2005/0228027 A1 describes certain sulfoximine compounds including some containing (6-alkylpyridin-3-yl)alkyl groups and their use in controlling insects. It has now been discovered that (6-haloalkylpyridin-3-yl)alkyl sulfoximines have greatly improved activity.

SUMMARY OF THE INVENTION

This invention concerns compounds useful for the control of insects, especially useful for the control of aphids and other sucking insects. More specifically, the invention concerns compounds of the formula (I)

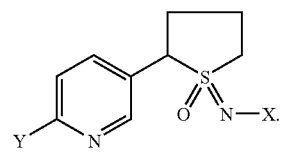

(I)

wherein
X represents $NO_2$, CN or $COOR^4$;
L represents a single bond or $R^1$, S and L taken together represents a 4-, 5- or 6-membered ring;
$R^1$ represents $(C_1-C_4)$ alkyl;
$R^2$ and $R^3$ independently represent hydrogen, methyl, ethyl, fluoro, chloro or bromo;
n is an integer from 0-3;
Y represents $(C_1-C_4)$ haloalkyl; and
$R^4$ represents $(C_1-C_3)$ alkyl.
Preferred compounds of formula (I) include the following classes:
(1) Compounds of formula (I) wherein X is $NO_2$ or CN, most preferably CN.
(2) Compounds of formula (I) wherein Y is $CF_3$.

(3) Compounds of formula (I) wherein $R^2$ and $R^3$ independently represent hydrogen, methyl or ethyl.
(4) Compounds of formula (I) wherein $R^1$, S and L taken together form a saturated 5-membered ring, and n is 0, i.e., having the structure

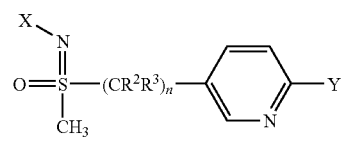

(5) Compounds of formula (I) wherein $R^1$ represents $CH_3$ and L represents a single bond, i.e., having the structure

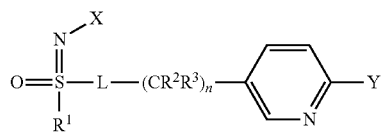

wherein n=1-3, most preferably n=1.

It will be appreciated by those skilled in the art that the most preferred compounds are generally those which are comprised of combinations of the above preferred classes.

The invention also provides new processes for preparing compounds of formula (I) as well as new compositions and methods of use, which will be described in detail hereinafter.

DETAILED DESCRIPTION OF THE INVENTION

Throughout this document, all temperatures are given in degrees Celsius, and all percentages are weight percentages unless otherwise stated.

Unless specifically limited otherwise, the term alkyl (including derivative terms such as alkoxy), as used herein, include straight chain, branched chain, and cyclic groups. Thus, typical alkyl groups are methyl, ethyl, 1-methylethyl, propyl, 1,1-dimethylethyl, and cyclopropyl. The term haloalkyl includes alkyl groups substituted with from one to the maximum possible number of halogen atoms, all combinations of halogens included. The term halogen includes fluorine, chlorine, bromine and iodine, with fluorine being preferred.

The compounds of this invention can exist as one or more stereoisomers. The various stereoisomers include geometric isomers, diastereomers and enantiomers. Thus the compounds of the present invention include racemic mixtures, individual stereoisomers and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials or by conventional resolution procedures.

The compounds of formula (Ia), wherein $R^1$, $R^2$, $R^3$, $R^4$, X, and Y are as previously defined and L is a single bond, can be prepared by the methods illustrated in Scheme A:

Scheme A

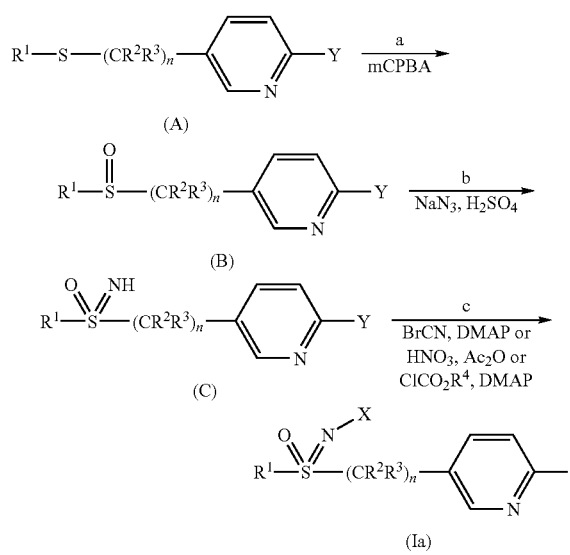

In step a of Scheme A, sulfide of formula (A) is oxidized with meta-chloroperoxybenzoic acid (mCPBA) in a polar solvent below 0° C. to provide sulfoxide of formula (B). In most cases, dichloromethane is the preferred solvent for oxidation.

In step b of Scheme A, sulfoxide (B) is iminated with sodium azide in the presence of concentrated sulfuric acid in an aprotic solvent under heating to provide sulfoximine of formula (C). In most cases, chloroform is the preferred solvent for this reaction.

In step c of Scheme A, the nitrogen of sulfoximine (C) can be either cyanated with cyanogen bromide in the presence of a base, or nitrated with nitric acid in the presence of acetic anhydride under mildly elevated temperature, or carboxylated with alkyl ($R^4$) chloroformate in the presence of base such as 4-dimethylaminopyridine (DMAP) to provide N-substituted sulfoximine (Ia). Base is required for efficient cyanation and carboxylation and the preferred base is DMAP, whereas sulfuric acid is used as catalyst for efficient nitration reaction.

The compounds of formula (Ia), wherein X represents CN and $R^1$, $R^2$, $R^3$, $R^4$ and Y are as previously defined, can be prepared by the mild and efficient method illustrated in Scheme B.

Scheme B

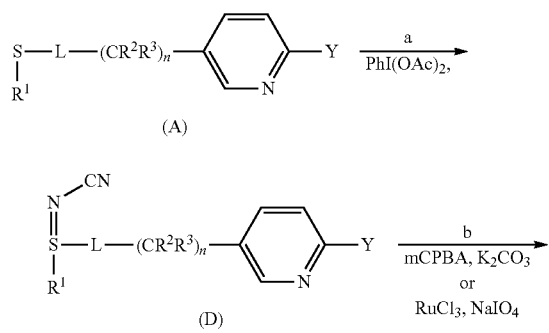

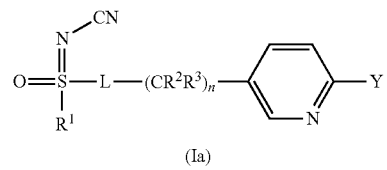

In step a of Scheme B, sulfide is oxidized with iodobenzene diacetate in the presence of cyanamide at 0° C. to give sulfilimine (D). The reaction can be carried out in a polar aprotic solvent like $CH_2Cl_2$.

In step b of Scheme B, the sulfilimine (D) is oxidized with mCPBA. A base such as potassium carbonate is employed to neutralize the acidity of mCPBA. Protic polar solvents such as ethanol and water are used to increase the solubility of the sulfilimine starting material and the base employed. The sulfilimine (D) can also be oxidized with aqueous sodium or potassium periodinate solution in the presence of catalyst ruthenium trichloride hydrate or similar catalyst. The organic solvent for this catalysis can be polar aprotic solvent such as $CH_2Cl_2$, chloroform, or acetonitrile.

The α-carbon of the N-substituted sulfoximine of formula (Ia), i.e., n=1, $R^3$=H in the ($CR^2R^3$) group adjacent to the N-substituted sulfoximine function can be further alkylated or halogenated ($R^5$) in the presence of a base such as potassium hexamethyldisilamide (KHMDS) to give N-substituted sulfoximines of formula (Ib), wherein $R^1$, $R^2$, $R^3$, $R^4$, X, L and Y are as previously defined and Z is an appropriate leaving group, as illustrated in Scheme C. The preferred leaving groups are iodide ($R^5$=alkyl), benzenesulfonimide ($R^5$=F), tetrachloroethene ($R^5$=Cl), and tetrafluoroethene ($R^5$=Br).

Scheme C

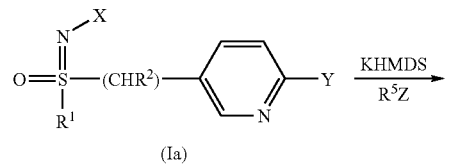

Sulfoximine compounds of formula (Ic) wherein $R^1$, S and L taken together form a saturated 4-, 5- or 6-membered ring and n=1 can be prepared by the methods illustrated in Scheme D wherein X and Y are as previously defined and m is 0, 1, or 2.

Scheme D

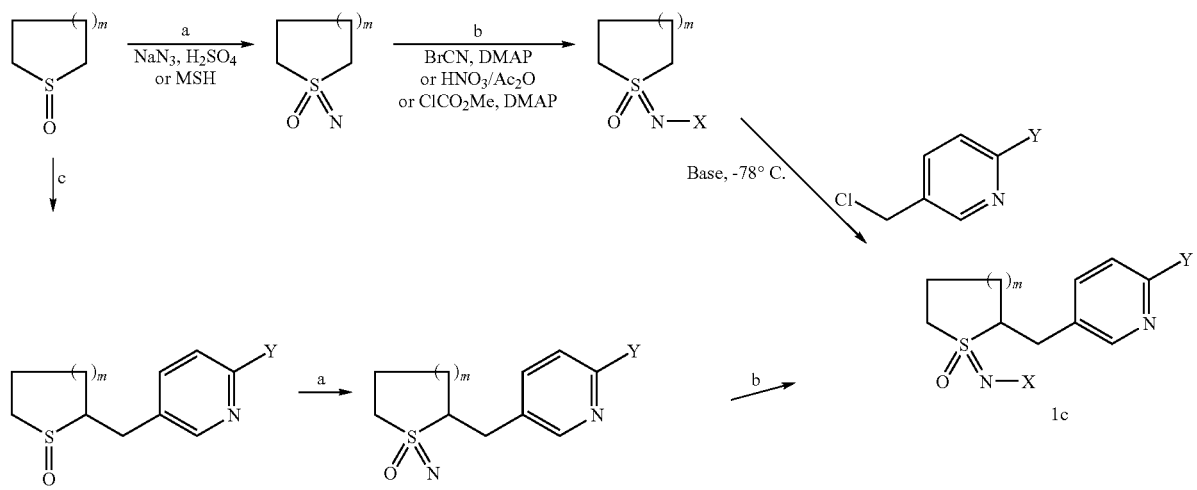

In step a of Scheme D, which is similar to step b of Scheme A, sulfoxide is iminated with sodium azide in the presence of concentrated sulfuric acid or with O-mesitylsulfonylhydroxylamine in a polar aprotic solvent to provide sulfoximine. Chloroform or dichloromethane are the preferred solvents.

In step b of Scheme D, similar to step c of Scheme A, the nitrogen of sulfoximine can be either cyanated with cyanogen bromide, or nitrated with nitric acid followed by treatment with acetic anhydride under refluxing conditions, or carboxylated with methyl chloroformate in the presence of base such as DMAP to provide N-substituted cyclic sulfoximine Base is required for efficient cyanation and carboxylation and the preferred base is DMAP, whereas sulfuric acid is used as catalyst for efficient nitration reaction.

In step c of Scheme D, the α-carbon of N-substituted sulfoximine can be alkylated with a heteroaromatic methyl halide in the presence of a base such as KHMDS or butyl lithium (BuLi) to give the desired N-substituted sulfoximines. The preferred halide can be bromide, chloride or iodide.

Alternatively, the compounds of formula (Ic) can be prepared by a first α-alkylation of sulfoxides to give α-substituted sulfoxides and then an imination of the sulfoxide followed by N-substitution of the resulting sulfoximine by using the steps c, a and b respectively as described above for Scheme D.

The starting sulfides (A) in Scheme A can be prepared in different ways as illustrated in Schemes E, F G, H, I and J.

In Scheme E, the sulfide of formula $(A_1)$, wherein $R^1$, $R^2$ and Y are as previously defined, n=1, and $R^3$=H, can be prepared from the chloride of formula (E) by nucleophilic substitution with the sodium salt of an alkyl thiol.

Scheme E

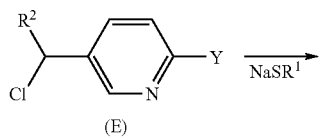

-continued

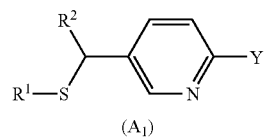

In Scheme F, the sulfide of formula $(A_2)$, wherein $R^1$, $R^2$ and Y are as previously defined, n=3, and $R^3$=H, can be prepared from the chloride of formula (F) by reacting with a 2-mono substituted methyl malonate in the presence of base such as potassium tert-butoxide to provide 2,2-disubstitued malonate, hydrolysis under basic conditions to form a diacid, decarboxylation of the diacid by heating to give a monoacid, reduction of the monoacid with borane-tetrahyrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

Scheme F

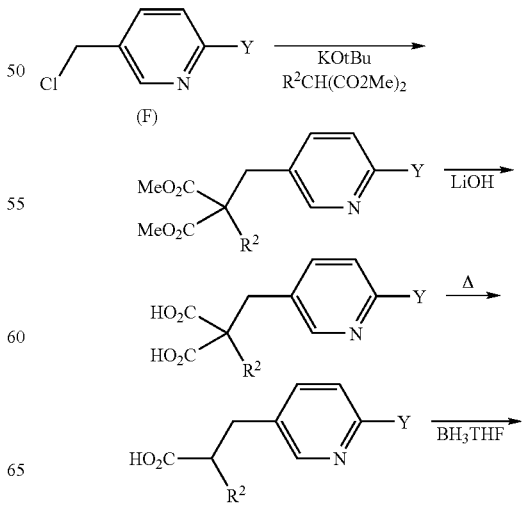

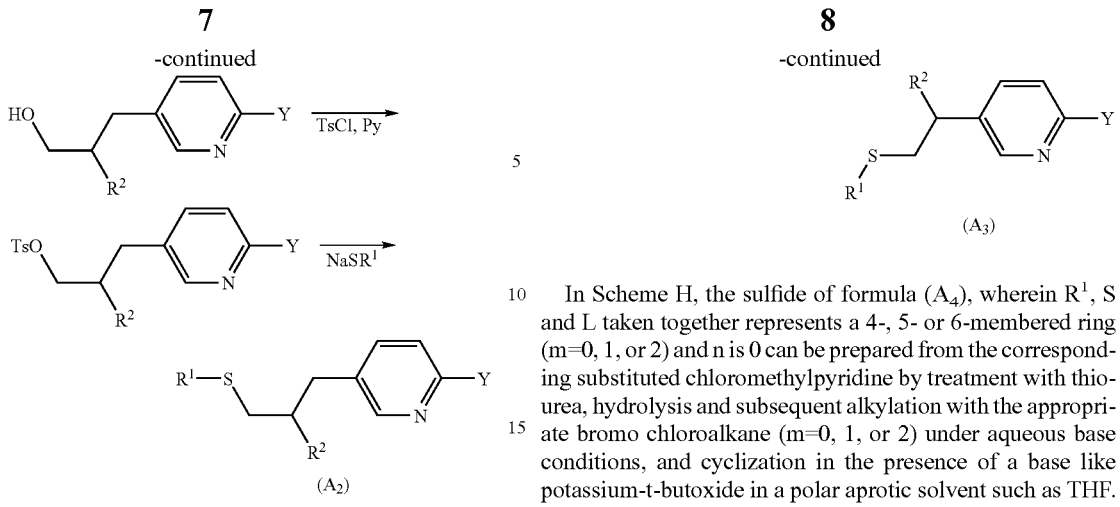

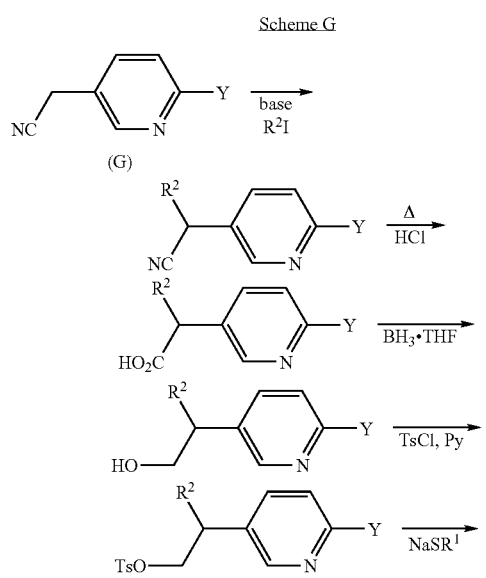

In Scheme G, the sulfide of formula (A₃), wherein R¹, R² and Y are as previously defined, n=2, and R³═H, can be prepared from the nitrile of formula (G) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

In Scheme H, the sulfide of formula (A₄), wherein R¹, S and L taken together represents a 4-, 5- or 6-membered ring (m=0, 1, or 2) and n is 0 can be prepared from the corresponding substituted chloromethylpyridine by treatment with thiourea, hydrolysis and subsequent alkylation with the appropriate bromo chloroalkane (m=0, 1, or 2) under aqueous base conditions, and cyclization in the presence of a base like potassium-t-butoxide in a polar aprotic solvent such as THF.

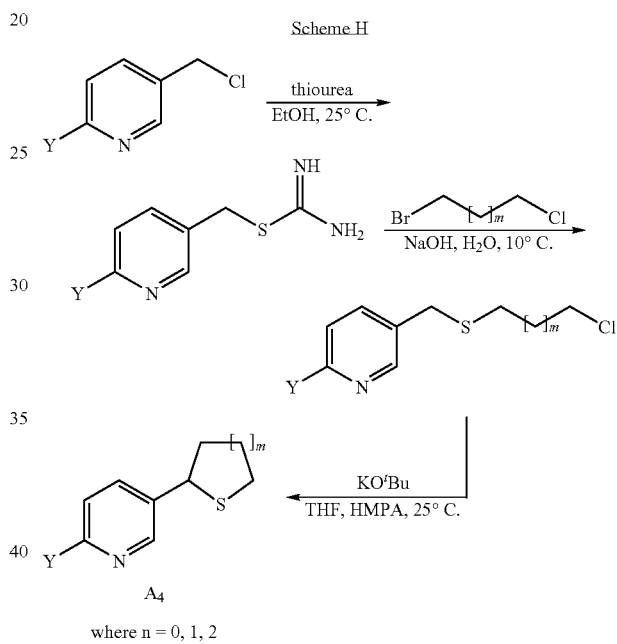

Sulfides of formula (A₁), wherein R¹, R²═CH₃, Y as previously defined, and R³═H, can be prepared alternatively via methods illustrated in Scheme I. Accordingly, the appropriate enone is coupled with dimethyl-aminoacrylonitrile and cyclized with ammonium acetate in DMF to yield the corresponding 6-substituted nicotinonitrile. Treatment with methylmagnesium bromide, reduction with sodium borohydride, chlorination with thionyl chloride, and nucleophilic substitution with the sodium salt of an alkyl thiol provide desired sulfides (A₁).

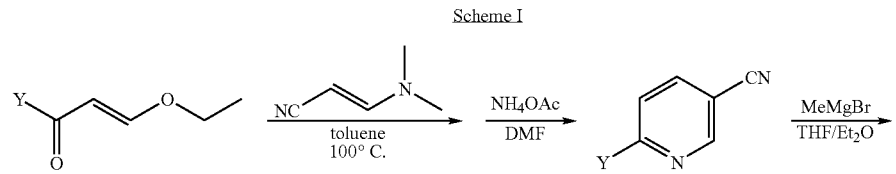

-continued

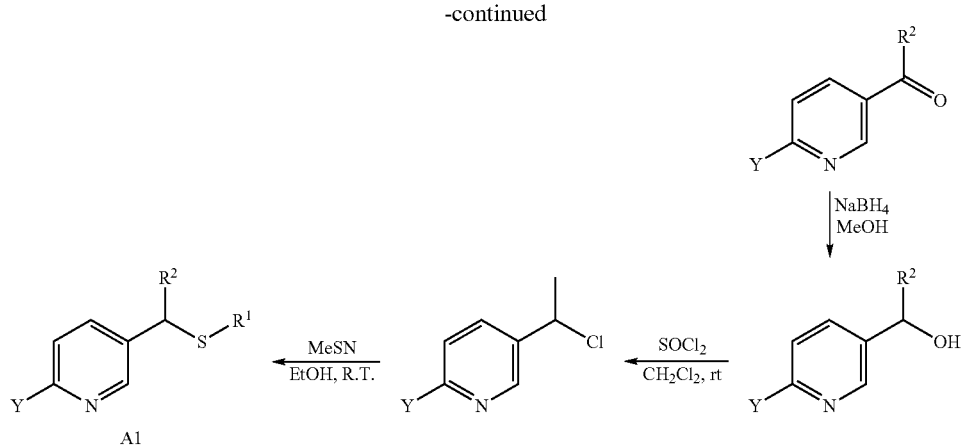

Sulfides of formula (A₁), wherein $R^1$=methyl or ethyl, $R^2$ and $R^3$ independently represent hydrogen, methyl or ethyl, and Y is as previously defined can be prepared via a variation of Scheme I, depicted in Scheme J, wherein enamines, formed from the addition of an amine, e.g., pyrrolidine, with the Michael adduct of certain sulfides with appropriately substituted α,β-unsaturated aldehydes, are coupled with substituted enones and cyclized with ammonium acetate in acetonitrile to yield the desired sulfides (A₁).

Scheme J

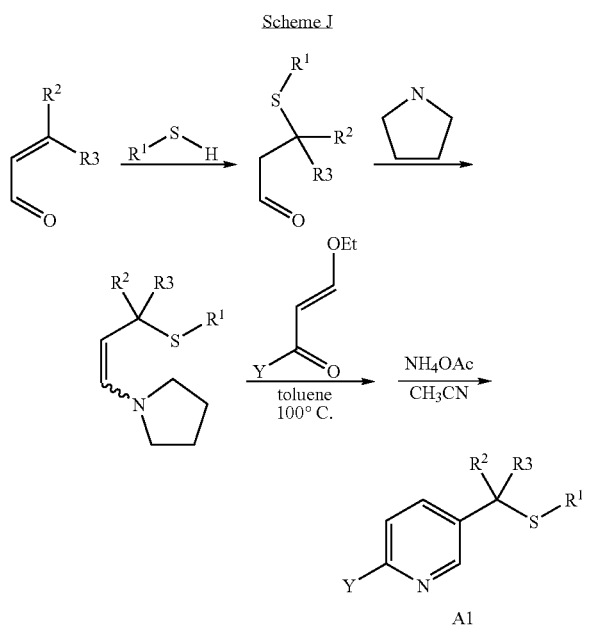

Sulfoximine compounds of the formula (Id) wherein n=2, $R^1$ and $R^2$ are hydrogen, L is a single bond, and X and Y are as previously defined can be prepared by the method illustrated in Scheme K. Dimethylsulfide is oxidized with iodobenzene diacetate in the presence of cyanamide at 0° C. to give the corresponding sulfilimine. The reaction can be carried out in a polar aprotic solvent like $CH_2Cl_2$ or THF. The sulfilimine is then oxidized with mCPBA. A base such as potassium carbonate is employed to neutralize the acidity of mCPBA. Protic polar solvents such as ethanol and water are used to increase the solubility of the sulfilimine starting material and the base employed. The α-carbon of the N-substituted sulfoximine can be alkylated with a heteroaromatic methyl halide in the presence of a base such as KHMDS or butyl lithium (BuLi) to give the desired N-substituted sulfoximine. The preferred halide can be bromide, chloride or iodide.

Scheme K

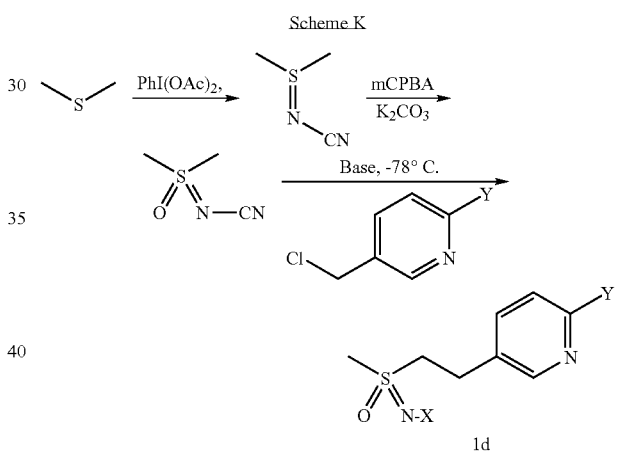

In Scheme L, sulfides of formula (A₁), wherein Y is a fluoroalkyl group, $R^1$ is as previously defined, and n=1 can be prepared from the 6-acylpyridine or 6-formyl pyridine by reaction with diethylaminosulfur trifluoride (DAST). Subsequent halogenation of the 3-methyl group with NBS followed by nucleophilic substitution with the sodium salt of an alkyl thiol furnishes the desired sulfide.

Scheme L

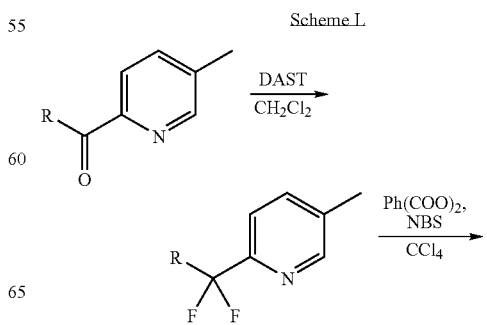

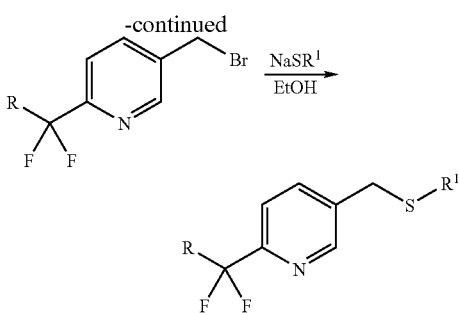
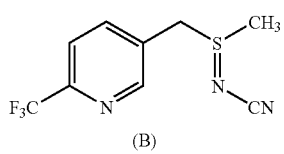

EXAMPLES

Example I

Preparation of [(6-trifluoromethylpyridin-3-yl)methyl](methyl)-oxido-$\lambda^4$-sulfanylidenecyanamide (1)

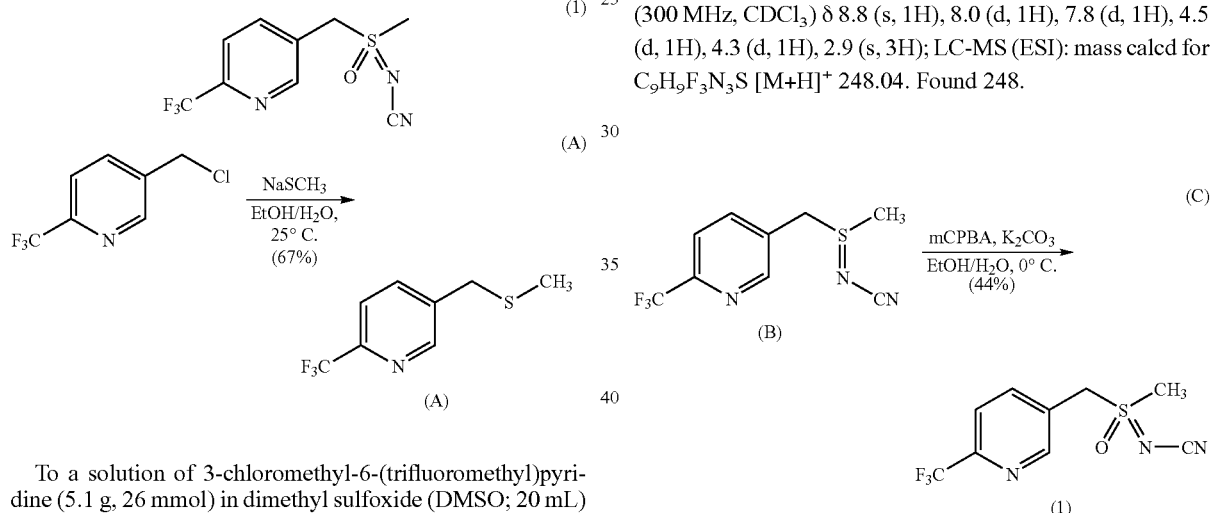

To a solution of 3-chloromethyl-6-(trifluoromethyl)pyridine (5.1 g, 26 mmol) in dimethyl sulfoxide (DMSO; 20 mL) was added in one portion sodium thiomethoxide (1.8 g, 26 mmol). A violent exothermic reaction was observed which resulted in the reaction turning dark. The reaction was stirred for 1 hr, then additional sodium thiomethoxide (0.91 g, 13 mmol) was added slowly. The reaction was stirred overnight, after which it was poured into H$_2$O and several drops of conc. HCl were added. The mixture was extracted with Et$_2$O (3×50 mL) and the organic layers combined, washed with brine, dried over MgSO$_4$ and concentrated. The crude product was purified by chromatography (Prep 500, 10% acetone/hexanes) to furnish the sulfide (A) as a pale yellow oil (3.6 g, 67%). $^1$H NMR (300 MHz, CDCl$_3$) δ 8.6 (s, 1H), 7.9 (d, 1H), 7.7 (d, 1H), 3.7 (s, 2H), 2.0 (s, 3H); GC-MS: mass calcd for C$_8$H$_8$F$_3$NS [M]$^+$ 207. Found 207.

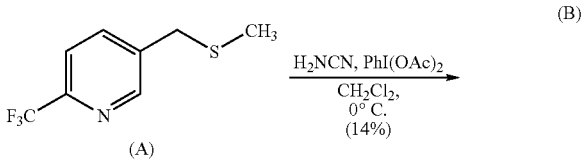

To a solution of sulfide (A) (3.5 g, 17 mmol) and cyanamide (1.4 mg, 34 mmol) in CH$_2$Cl$_2$ (30 mL) at 0° C. was added iodobenzenediacetate (11.0 g, 34 mmol) all at once. The reaction was stirred for 30 min, then allowed to warm to room temperature overnight. The mixture was diluted with CH$_2$Cl$_2$ (50 mL) and washed with H$_2$O. The aqueous layer was extracted with ethyl acetate (4×50 mL), and the combined CH$_2$Cl$_2$ and ethyl acetate layers dried over MgSO$_4$ and concentrated. The crude product was triturated with hexanes and purifed by chromatography (chromatotron, 60% acetone/hexanes) to furnish the sulfilimine (B) as a yellow gum (0.60 g, 14%). IR (film) 3008, 2924, 2143, 1693 cm$^{-1}$; $^1$H NMR (300 MHz, CDCl$_3$) δ 8.8 (s, 1H), 8.0 (d, 1H), 7.8 (d, 1H), 4.5 (d, 1H), 4.3 (d, 1H), 2.9 (s, 3H); LC-MS (ESI): mass calcd for C$_9$H$_9$F$_3$N$_3$S [M+H]$^+$ 248.04. Found 248.

To a solution of m-chloroperbenzoic acid (mCPBA; 80%, 1.0 g, 4.9 mmol) in EtOH (10 mL) at 0° C. was added a solution of K$_2$CO$_3$ (1.4 g, 10 mmol) in H$_2$O (7 mL). The solution was stirred for 20 min, then a solution of sulfilimine (B) (0.60 g, 2.4 mmol) in EtOH (20 mL) was added all at once. The reaction was stirred at 0° C. for 30 min, then allowed to warm to room temperature over the course of 1 hr. The reaction was then quenched with aq. sodium bisulfite and the mixture was concentrated to remove ethanol. The resulting mixture was extracted with CH$_2$Cl$_2$ and the combined organic layers dried over MgSO$_4$ and concentrated. The crude product was purified by chromatography (chromatotron, 50% acetone/hexanes) to furnish the sulfoximine (1) as an off-white solid (0.28 g, 44%). Mp=135-137° C.; $^1$H NMR (300 MHz, CDCl$_3$) δ 8.8 (s, 1H), 8.1 (d, 1H), 7.8 (d, 1H), 4.7 (m, 2H), 3.2 (s, 3H); LC-MS (ELSD): mass calcd for C$_9$H$_9$F$_3$N$_3$OS [M+H]$^+$ 264.04. Found 263.92.

Example II

Preparation of [1-(6-trifluoromethylpyridin-3-yl)ethyl](methyl)-oxido-$\lambda^4$-sulfanylidenecyanamide (2)

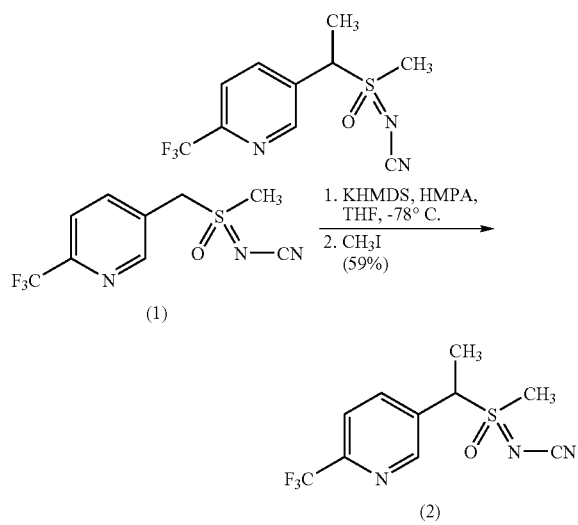

To a solution of sulfoximine (1) (50 mg, 0.19 mmol) and hexamethylphosphoramide (HMPA; 17 μL, 0.10 mmol) in tetrahydrofuran (THF; 2 mL) at −78° C. was added potassium hexamethyldisilazane (KHMDS; 0.5 M in toluene, 420 μL, 0.21 mmol) dropwise. The solution was stirred at −78° C. for an additional 20 min, after which iodomethane (13 μL, 0.21 mmol) was added. The reaction was allowed to warm to room temperature over the course of 1 hr, after which it was quenched with satd. aq. NH$_4$Cl and extracted with CH$_2$Cl$_2$. The organic layer was dried over Na$_2$SO$_4$, concentrated, and the crude product purified by chromatography (chromatotron, 70% acetone/CH$_2$Cl$_2$) to furnish the sulfoximine (2) as a 2:1 mixture of diastereomers (colorless oil; 31 mg, 59%). $^1$H NMR (300 MHz, CDCl$_3$) δ (major diastereomer) 8.8 (s, 1H), 8.1 (d, 1H), 7.8 (d, 1H), 4.6 (q, 1H), 3.0 (s, 3H), 2.0 (d, 3H); (minor diastereomer) 8.8 (s, 1H), 8.1 (d, 1H), 7.8 (d, 1H), 4.6 (q, 1H), 3.1 (s, 3H), 2.0 (d, 3H); LC-MS (ELSD): mass calcd for C$_{10}$H$_{10}$F$_3$N$_3$OS [M+H]$^+$ 278.06. Found 278.05.

Example III

Preparation of 2-(6-trifluoromethylpyridin-3-yl)-1-oxido-tetrahydro-1H-1$\lambda^4$-thien-1-ylidenecyanamide (3)

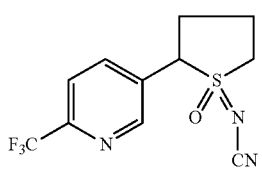

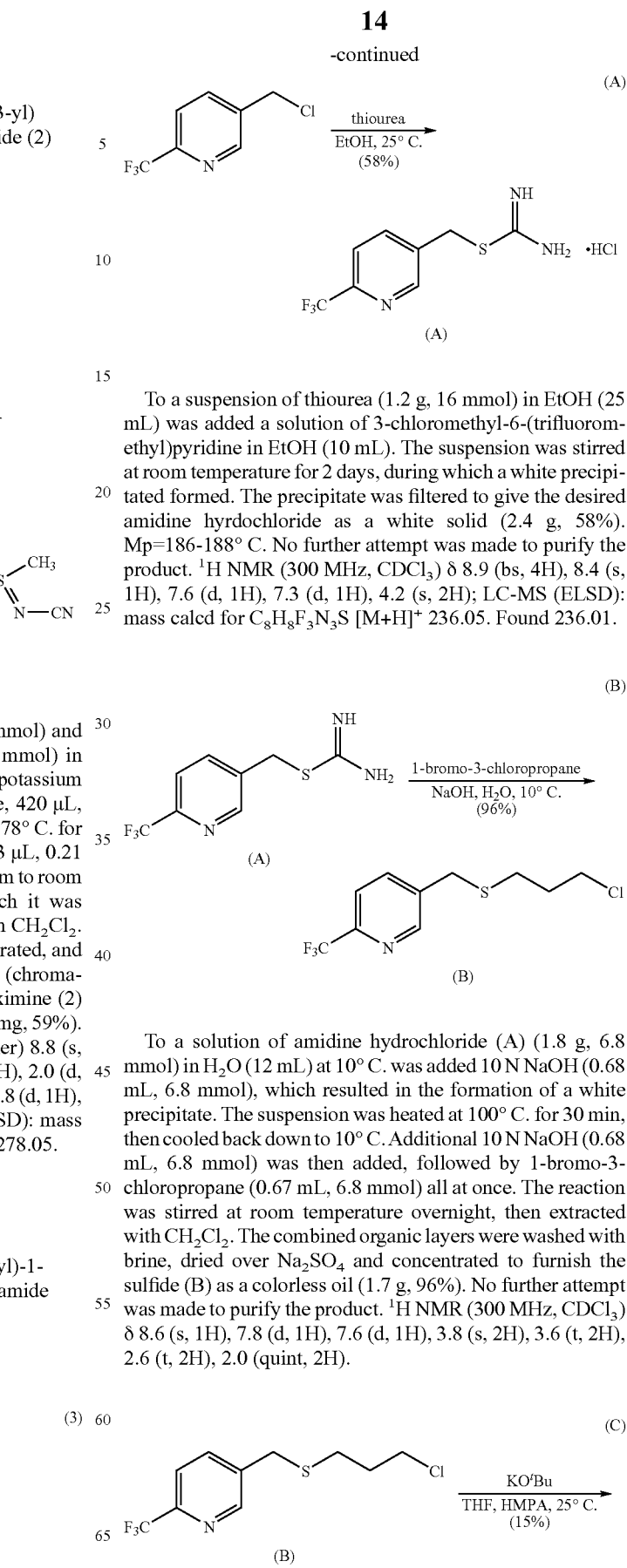

To a suspension of thiourea (1.2 g, 16 mmol) in EtOH (25 mL) was added a solution of 3-chloromethyl-6-(trifluoromethyl)pyridine in EtOH (10 mL). The suspension was stirred at room temperature for 2 days, during which a white precipitated formed. The precipitate was filtered to give the desired amidine hyrdochloride as a white solid (2.4 g, 58%). Mp=186-188° C. No further attempt was made to purify the product. $^1$H NMR (300 MHz, CDCl$_3$) δ 8.9 (bs, 4H), 8.4 (s, 1H), 7.6 (d, 1H), 7.3 (d, 1H), 4.2 (s, 2H); LC-MS (ELSD): mass calcd for C$_8$H$_8$F$_3$N$_3$S [M+H]$^+$ 236.05. Found 236.01.

To a solution of amidine hydrochloride (A) (1.8 g, 6.8 mmol) in H$_2$O (12 mL) at 10° C. was added 10 N NaOH (0.68 mL, 6.8 mmol), which resulted in the formation of a white precipitate. The suspension was heated at 100° C. for 30 min, then cooled back down to 10° C. Additional 10 N NaOH (0.68 mL, 6.8 mmol) was then added, followed by 1-bromo-3-chloropropane (0.67 mL, 6.8 mmol) all at once. The reaction was stirred at room temperature overnight, then extracted with CH$_2$Cl$_2$. The combined organic layers were washed with brine, dried over Na$_2$SO$_4$ and concentrated to furnish the sulfide (B) as a colorless oil (1.7 g, 96%). No further attempt was made to purify the product. $^1$H NMR (300 MHz, CDCl$_3$) δ 8.6 (s, 1H), 7.8 (d, 1H), 7.6 (d, 1H), 3.8 (s, 2H), 3.6 (t, 2H), 2.6 (t, 2H), 2.0 (quint, 2H).

-continued

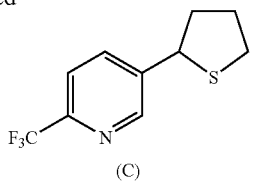

(C)

To a suspension of potassium tert-butoxide (1.5 g, 13 mmol) in THF (12 mL) was added HMPA (1.7 mL, 10 mmol) followed by a solution of sulfide (B) (1.8 g, 6.7 mmol) in THF (3 mL) dropwise. The reaction was allowed to stir at room temperature overnight, followed by concentration and purification by chromatography (Biotage, 40% EtOAc/hexanes) to furnish cyclized product (C) as an orange oil (230 mg, 15%). $^1$H NMR (300 MHz, CDCl$_3$) δ 8.7 (s, 1H), 8.0 (d, 1H), 7.6 (d, 1H), 4.6 (dd, 1H), 3.2 (m, 1H), 3.1 (m, 1H), 2.5 (m, 1H), 2.3 (m, 1H), 2.1-1.9 (m, 2H).

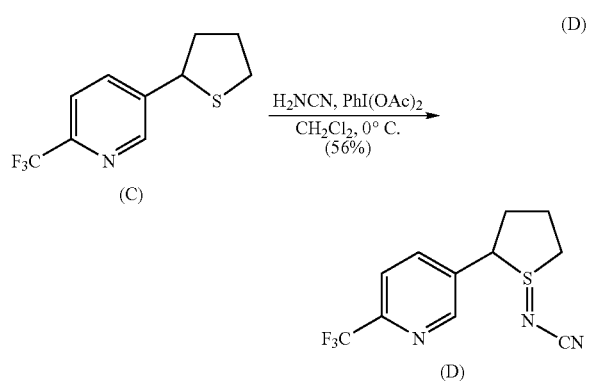

To a solution of sulfide (C) (230 mg, 0.99 mmol) and cyanamide (83 mg, 2.0 mmol) in CH$_2$Cl$_2$ (5 mL) at 0° C. was added iodobenzenediacetate (350 mg, 1.1 mmol) all at once. The reaction was stirred for 3 hr, then concentrated and the crude product purified by chromatography (chromatotron, 50% acetone/hexanes) to furnish the sulfilimine (D) as an orange oil (150 mg, mixture of diastereomers, 56%). $^1$H NMR (300 MHz, CDCl$_3$) δ 8.8 (s, 1H), 7.9 (d, 1H), 7.8 (d, 1H), 4.8 (dd, 1H), 3.5 (m, 2H), 2.9-2.7 (m, 2H), 2.6 (m, 1H), 2.3 (m, 1H).

To a solution of mCPBA (80%, 180 mg, 0.82 mmol) in EtOH (3 mL) at 0° C. was added a solution of K$_2$CO$_3$ (230 mg, 1.7 mmol) in H$_2$O (1.5 mL). The solution was stirred for 20 min, then a solution of sulfilimine (D) (150 mg, 0.55 mmol) in EtOH (2 mL) was added all at once. The reaction was stirred at 0° C. for 45 min, after which the solvent was decanted into a separate flask and concentrated to give a white solid. The solid was slurried in CHCl$_3$, filtered, and concentrated to furnish pure sulfoximine (3) as a colorless oil (72 mg, 44%). $^1$H NMR (300 MHz, CDCl$_3$) δ (1.5:1 mixture of diastereomers) 8.8 (s, 2H), 8.0 (d, 2H), 7.8 (d, 2H), 4.7 (q, 1H), 4.6 (q, 1H), 4.0-3.4 (m, s, 4H), 3.0-2.4 (m, 8H); LC-MS (ELSD): mass calcd for C$_{11}$H$_{11}$F$_3$N$_3$OS [M+H]$^+$ 290.06. Found 289.99.

Example IV

Preparation of (1-{6-[chloro(difluoro)methyl]pyridin-3-yl}ethyl)(methyl)-oxido-λ$^4$-sulfanylidenecyanamide (4)

(4)

(A)

(3E)-1-Chloro-4-ethoxy-1,1-difluorobut-3-en-2-one (7.36 g, 40 mmol) was dissolved in dry toluene (40 mL) and treated with 3-dimethylaminoacrylonitrile (4.61 g, 48 mmol) at room temperature. The solution was heated at about 100° C. for 3.5 hr. The solvent was then removed under reduced pressure and the remaining mixture was re-dissolved in DMF (20 mL), treated with ammonium acetate (4.62 g, 60 mmol) and stirred at room temperature overnight. Water was added to the reaction mixture and the resulting mixture was extracted with ether-CH$_2$CH$_2$ (1:2, v/v) twice. The combined organic layer was washed with brine, dried, filtered and concentrated. The residue was purified on silica gel to give 3.1 g of 6-[chloro(difluoro)methyl]nicotinonitrile (A) as light colored oil in 41% yield. GC-MS: mass calcd for C$_7$H$_3$ClF$_2$N$_2$ [M]$^+$ 188. Found 188.

(B)

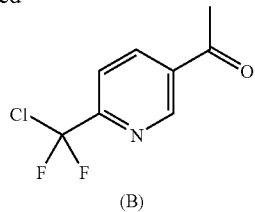

(B)

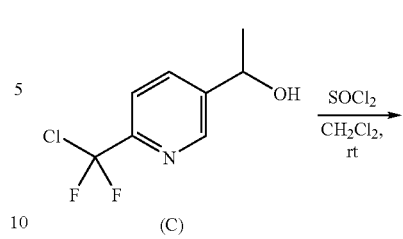

(C)

6-[Chloro(difluoro)methyl]nicotinonitrile (A) (3.0 g, 15.8 mmol) was dissolved in anhydrous ether (25 mL) and cooled in an ice-water bath. A solution of 3 M of methylmagnesium bromide in hexane (6.4 mL, 19 mmol) was added through a syringe. After the addition was over, the mixture was stirred at 0° C. for 5 hr and then at room temperature for 10 hr. The reaction was quenched slowly with 1 N citric acid aqueous solution at 0° C. and the resulting mixture was stirred at room temperature for 1 hr. The pH was adjusted back to pH 7 with saturated $NaHCO_3$ aqueous solution. The two phases were separated and the aqueous phase was extracted with ethyl acetate twice. The combined organic layer was washed with brine, dried over anhydrous $Na_2SO_4$, filtered, and concentrated. The remaining mixture was purified on silica gel eluted with 15% acetone in hexane to give 0.88 g of the desired product 1-{6-[chloro(difluoro)methyl]pyridin-3-yl}-ethanone (B) as brownish oil in 30% yield. GC-MS: mass calcd for $C_8H_6ClF_2NO$ $[M]^+$ 205. Found 205.

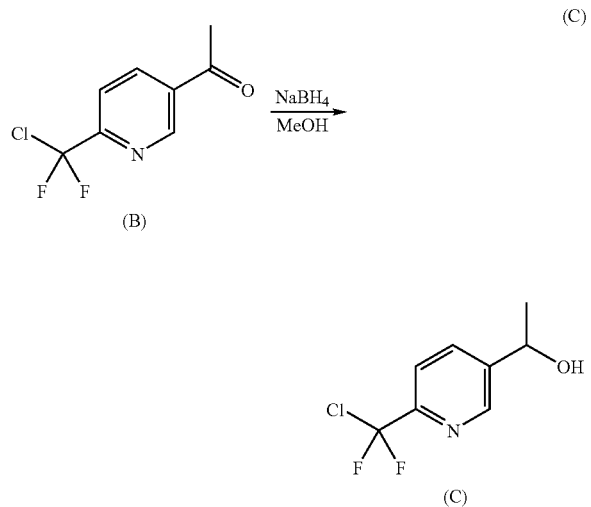

To a solution of 1-{6-[chloro(difluoro)methyl]pyridin-3-yl}ethanone (B) (0.85 g, 4.14 mmol) in MeOH (10 mL) at 0° C. was added $NaBH_4$ (0.16 g, 4.14 mmol). The mixture was stirred for 30 min and 2 M HCl aqueous solution was added until pH reached 7. Solvent was removed under reduced pressure and the remaining mixture was extracted with $CH_2Cl_2$ (2×50 mL). The combined organic layer was dried over anhydrous $Na_2SO_4$, filtered, concentrated, and dried in vacuo to give 0.798 g of analytically pure 1-{6-[chloro(difluoro)methyl]-pyridin-3-yl}ethanol (C) on GC-MS as a light yellow oil in 93% yield. GC-MS: mass calcd for $C_8H_6ClF_2NO$ $[M]^+$ 207. Found 207.

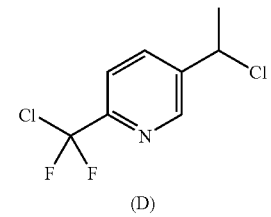

(D)

To a solution of 1-{6-[chloro(difluoro)methyl]-pyridin-3-yl}ethanol (0.78 g, 3.77 mmol) in $CH_2Cl_2$ (40 mL) was added thionyl chloride (0.54 mL, 7.54 mmol) dropwise at room temperature. After 1 hr, the reaction was quenched slowly with saturated $NaHCO_3$ aqueous solution and the two phases were separated. The organic layer was dried over $Na_2SO_4$, filtered, concentrated, and dried in vacuum to give 0.83 g of the crude 2-[chloro(difluoro)methyl]-5-(1-chloroethyl)pyridine (D) as brown oil in 98% yield, which was directly used for the next step reaction. GC-MS: mass calcd for $C_8H_7Cl_2F_2N$ $[M]^+$ 225. Found 225.

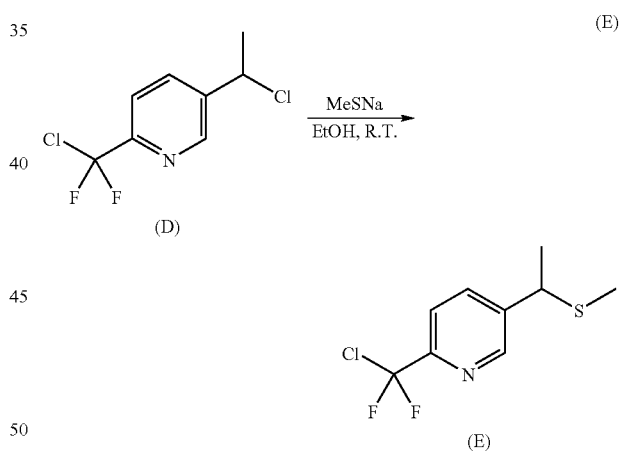

To a solution of 2-[chloro(difluoro)methyl]-5-(1-chloroethyl)pyridine (D) (0.81 g, 3.6 mmol) in ethanol (10 mL) was added sodium thiomethoxide (0.52 g, 7.4 mmol) under stirring in one portion at 0° C. After 10 min, the mixture was allowed to warm to room temperature and stirred overnight. The solvent ethanol was then removed under reduced pressure and the residue was re-taken into ether/$CH_2Cl_2$ and brine. The two phases were separated and the organic layer was extracted with $CH_2Cl_2$ one more time. The combined organic layer was dried over anhydrous $Na_2SO_4$, filtered, concentrated, purified on silica gel using 5% ethyl acetate in hexane to give 0.348 g of the 2-[chloro(difluoro)methyl]-5-[1-(methylthio)ethyl]pyridine (E) in 40% yield GC-MS: mass calcd for $C_9H_{10}ClF_2NS$ $[M]^+$ 237. Found 237.

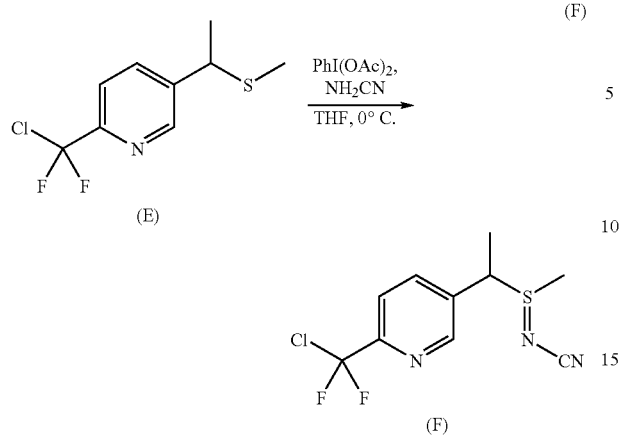

To a stirred solution of 2-[chloro(difluoro)methyl]-5-[1-(methylthio)-ethyl]pyridine (E) (0.32 g, 1.35 mmol) and cyanamide (0.058 g, 1.35 mmol) in THF (7 mL) was added iodobenzene diacetate (0.44 g, 1.35 mmol) in one portion at 0° C. and the resulting mixture was stirred at this temperature for 1 hr and then at room temperature for 2 hr. The solvent was then removed under reduced pressure and the resulting mixture was dissolved in CH$_2$Cl$_2$, washed with half-saturated brine, dried over anhydrous Na$_2$SO$_4$, filtered, concentrated, and purified on silica gel using 50% acetone in hexane to give 0.175 g of (1-{6-[chloro-(difluoro)methyl]pyridin-3-yl}ethyl)(methyl)-λ$^4$-sulfanylidenecyanamide (F) as light-yellow oil in 48% yield. $^1$H NMR (300 MHz, CDCl$_3$) δ 8.71 (d, J=1.8 Hz, 1H), 7.91 (dd, J=8.4, 1.8 Hz, 1H) 7.78 (d, J=8.4 Hz, 1H), 4.42 (q, J=6.9 Hz, 1H), 2.64 (s, 3H), 1.92 (d, J=6.9 Hz, 3H); LC-MS: mass calcd for C$_{10}$H$_{10}$ClF$_2$N$_3$S [M+1]$^+$ 278. Found 278.

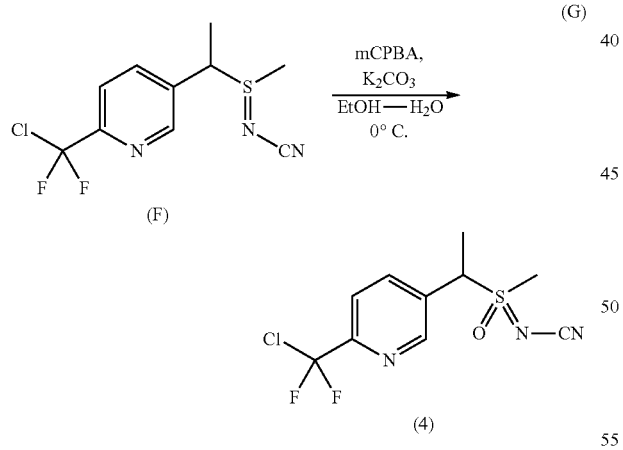

To a stirred solution of (1-[6-[chloro(difluoro)methyl]pyridin-3-yl]ethyl)-(methyl)-λ$^4$-sulfanylidenecyanamide (F) (0.16 g, 0.6 mmol) in ethanol (10 mL) was added 20% potassium carbonate aqueous solution (1.24 g, 1.8 mmol) at 0° C. under stirring. After 10 min stirring, 80% mCPBA (0.19 g, ca 0.9 mmol) was added to the mixture, which was stirred at 0° C. for 2 hr after which the reaction was quenched with a spatula of solid sodium thiosulfate. Most of the solvent ethanol was removed under reduced pressure and an aqueous saturated NaHCO$_3$-brine (1:1, v/v) solution was added and the mixture extracted with chloroform three times. The combined organic layer was dried over Na$_2$SO$_4$, filtered and concentrated. The residue was purified on silica gel using 35-50% acetone in hexane as eluent to give 0.092 g of the product (1-{6-[chloro(difluoro)-methyl]pyridin-3-yl}ethyl)(methyl)oxido-λ$^4$-sulfanylidenecyanamide (4) as colorless oil in 57% yield. $^1$H NMR (300 MHz, CDCl$_3$) δ 8.79 (s, 1H), 8.09 (d, J=8.1 Hz, 1H), 7.80 (d, J=8.1 Hz, 1H), 4.73 (q, J=7.2 Hz, 1H), 3.16 and 3.11 (2 s, 3H, a mixture of two diastereomeric α-CH$_3$ groups between the sulfoximine and the pyridine tail), 2.00 (d, J=7.2 Hz, 3H); LC-MS: mass calcd for C$_{10}$H$_{10}$ClF$_2$N$_3$OS [M−1]$^+$ 292. Found 292.

Example V

Preparation of [1-(6-trichloromethylpyridin-3-yl)ethyl](methyl)-oxido-λ$^4$-sulfanylidenecyanamide (5)

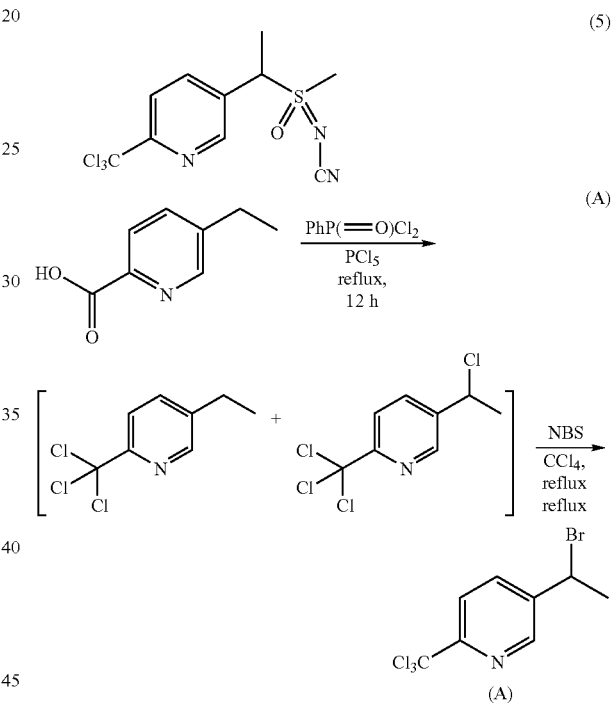

A mixture of 5-ethylpyridine-2-carboxylic acid (1.98 g, 13 mmol), phenyl-phosphonic dichloride (2.8 g, 14.3 mmol), phosphorus pentachloride (7.7 g, 32 mmol) was stirred and slowly heated. Once a clear yellow liquid was formed, the mixture was heated to reflux overnight. After cooling, the volatiles were removed under reduced pressure. The residue was carefully poured into saturated sodium carbonate aqueous solution cooled in an ice-water bath. The aqueous phase was then extracted with CH$_2$Cl$_2$ two times. The combined organic layer was washed with brine, dried over anhydrous Na$_2$SO$_4$, filtered, concentrated, and partially purified on silica gel eluted with 10% EtOAc in hexane to give 2.7 g of crude product containing both 5-ethyl-2-(trichloromethyl)pyridine and 5-(1-chloro-ethyl)-2-(trichloromethyl)pyridine in an approximate 3:1 ratio (GC data, masses calcd for C$_8$H$_8$Cl$_3$N and C$_8$H$_7$Cl$_4$N [M]$^+$ 223 and 257 respectively. Found 223 and 257 respectively).

A mixture of the above-mentioned crude product (2.6 g) in carbon tetrachloride (100 mL) was then treated with 80% of N-bromosuccinimide (1.9 g, 11 mmol) and benzoylperoxide (0.66 g, 0.275 mmol) and then refluxed overnight. The solid was filtered off, the filtrate concentrated and the resulting residue purified on silica gel using 4% EtOAc in hexane to give 1.0 g of the desired product 5-(1-bromoethyl)-2-(trichloromethyl)pyridine (A) as a yellow solid. The combined yield for the two steps was 25%. GC-MS: mass calcd for $C_8H_7BrCl_3N$ $[M-1-Cl]^+$ 266. Found 266.

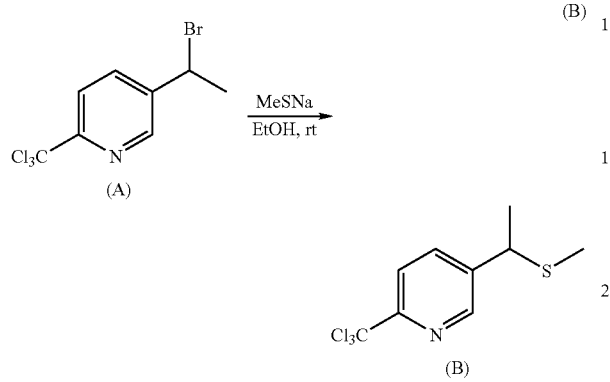

A solution of 5-(1-bromoethyl)-2-(trichloromethyl)pyridine (A) (0.95 g, 3.14 mmol) in ethanol (15 mL) was treated with sodium thiomethoxide (0.44 g, 6.29 mmol) portionwise at 0° C. The mixture was stirred at room temperature overnight. The solvent ethanol was then removed under a reduced pressure and the residue was re-taken into $CH_2Cl_2$ and brine. The two phases were separated and the organic layer was dried over anhydrous $Na_2SO_4$, filtered, concentrated. The residue was purified on silica gel using 5% EtOAc in hexane to give 0.57 g of the partially pure 5-[1-(methylthio)ethyl]-2-(trichloromethyl)pyridine (B) in 67% crude yield. GC-MS: mass calcd for $C_9H_{10}Cl_3NS$ $[M]^+$ 269. Found 269.

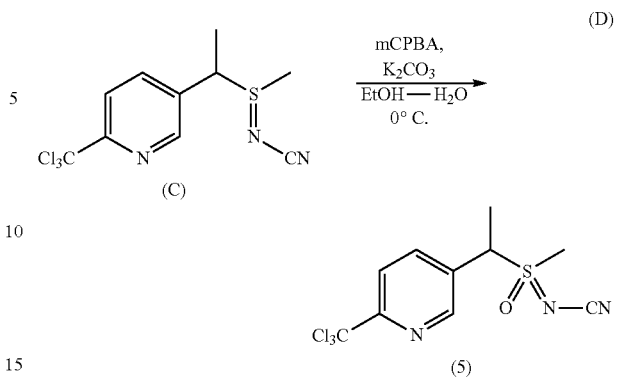

To a stirred solution of 5-[1-(methylthio)ethyl]-2-(trichloromethyl)-pyridine (B) (0.55 g, 2.3 mmol) and cyanamide (0.097 g, 2.3 mmol) in THF (7 mL) cooled to 0° C. was added iodobenzene diacetate (0.75 g, 2.3 mmol) in one portion. The resulting mixture was stirred at 0° C. for 1 hr and then at room temperature for 2 hr. The solvent was removed in vacuo and the resulting mixture was purified on silica gel using 50% acetone in hexane to give 0.254 g of (1E)-methyl{1-[6-(trichloromethyl)pyridin-3-yl]ethyl}-λ⁴-sulfanylidenecyanamide (C) as an off-white solid in 40% yield. ¹H NMR for the diastereomeric mixture (300 MHz, $d_6$-acetone) δ 8.87 (s, 1H), 8.21-8.25 (m, 2H), 4.65-4.76 (m, 1H), 2.86-2.66 (m, 3H), 1.88-1.92 (m, 3H).

To a stirred solution of (1E)-methyl{1-[6-(trichloromethyl)pyridin-3-yl]ethyl}-λ⁴-sulfanylidenecyanamide (C) (0.20 g, 0.65 mmol) in ethanol (15 mL) was added 20% aqueous potassium carbonate solution (1.3 mL) at 0° C., followed by addition of 80% mCPBA. The resulting mixture was stirred for 2 hr at 0° C. and then quenched with solid sodium thiosulfate. Most of the solvent was evaporated and 1:1 aqueous saturated $NaHCO_3$-brine (v/v) was added and the mixture was extracted with chloroform three times. The combined organic layer was dried over anhydrous $Na_2SO_4$, filtered and concentrated. The residue was purified on silica gel using 40% acetone in hexane to give 0.10 g of [1-(6-trichloromethylpyridin-3-yl)ethyl](methyl)-oxido-λ⁴-sulfanylidene-cyanamide (5) as colorless oil in 50% yield. ¹H NMR (300 MHz, $CDCl_3$) δ 8.83 (s, 1H), 8.12-8.23 (m, 1H), 5.15 (q, 1H), 3.37 and 3.28 (2 s, 3H, a mixture of two diastereomeric α-$CH_3$ groups between the sulfoximine and the pyridine tail), 2.03 (d, 3H); LC-MS: mass calcd for $C_{10}H_{12}Cl_3N_3OS$ $[M+1]^+$ 328. Found 328.

Example VI

Preparation of [2-(6-trifluoromethylpyridin-3-yl) ethyl](methyl)-oxido-λ⁴-sulfanylidenecyanamide (6)

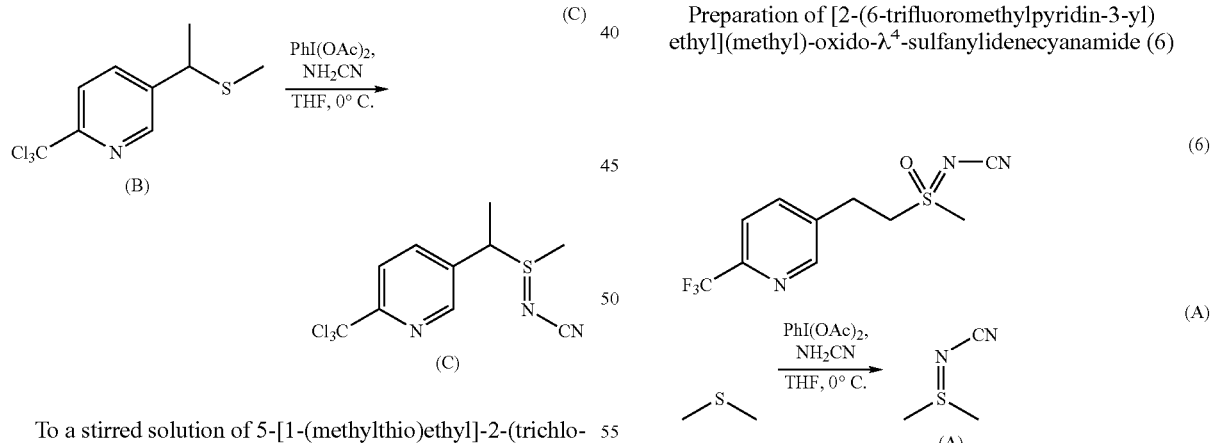

To a solution of dimethylsulfide (10.0 g, 161 mmol) and cyanamide (6.7 g, 161 mmol) in THF (500 mL) at 0° C. was added iodobenzenediacetate (51.8 g, 161 mmol) all at once. Let stir at 0° C. for 30 min, then allowed reaction to warm to room temperature overnight. The reaction was concentrated and purified by passing through a silica gel plug, first with 100% hexanes, then with 100% acetone, furnishing sulfilimine (A) as a colorless oil=13.4 g (82%). ¹H NMR (300 MHz, $CDCl_3$) δ 2.8 (s, 6H); GC-MS: mass calcd for $C_3H_6N_2S$ $[M]^+$, 102. Found 102.

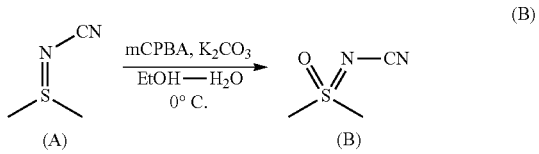

(B)

To a solution mCPBA (80%, 25.3 g, 147 mmol) in EtOH (450 mL) at 0° C. was added solution of $K_2CO_3$ (40.6 g, 294 mmol) in $H_2O$ (340 mL). After 20 min, sulfilimine (10.0 g, 98 mmol) in EtOH (150 mL) was added all at once. The suspension was stirred at 0° C. for 90 min, after which the crude reaction mixture was concentrated to remove EtOH, then extracted with $CH_2Cl_2$ (3×). The combined organic layers were washed with satd aq $NaHCO_3$ soln (3×), dried over $Na_2SO_4$ and concentrated to furnish sulfoximine (B) as a yellow solid=1.310 g (10%). $^1H$ NMR (300 MHz, $CDCl_3$) δ 3.4 (s, 6H); GC-MS: mass calcd for $C_3H_6N_2OS$ $[M]^+$, 118. Found 118.

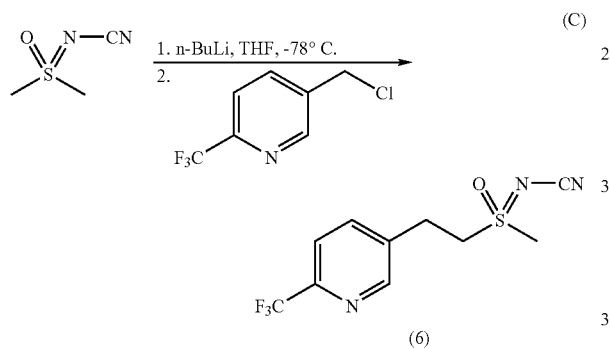

(6)

To a solution of sulfoximine (100 mg, 0.85 mmol) in THF (2 mL) at −78° C. was added nBuLi (2.5 M, 340 μL, 0.85 mmol) dropwise. The solution was let solution stir for 20 min, then 5-(chloromethyl)-2-trifluoromethylpyridine (170 mg, 0.85 mmol) was added. The solution was let solution stir at −78° C. for additional 2 h, then quenched with satd aq ammonium chloride and extracted with $CH_2Cl_2$. The combined organic extracts were dried over sodium sulfate, concentrated and purified by flash chromatography (40% EtOAc/80% hexanes) to furnish [2-(6-trifluoromethylpyridin-3-yl)ethyl](methyl)-oxido-$\lambda^4$-sulfanylidene-cyanamide (6) as a yellow solid=14.5 mg (6%); mp=83-87° C. $^1H$ NMR (300 MHz, $CDCl_3$) δ 8.69 (d, 1H), 7.85 (dd, 1H), 7.74 (d, 1H), 3.58-3.79 (m, 2H), 3.38-3.46 (m, 2H), 3.30 (s, 3H); LC-MS (ELSD): mass calcd for $C_{10}H_{11}F_3N_3OS$ $[M+H]^+$, 278. Found 278.

Example VII

Preparation of [(6-difluoromethylpyridin-3-yl)methyl](methyl)-oxido-$\lambda^4$-sulfanylidenecyanamide (7)

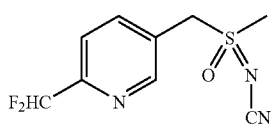

(7)

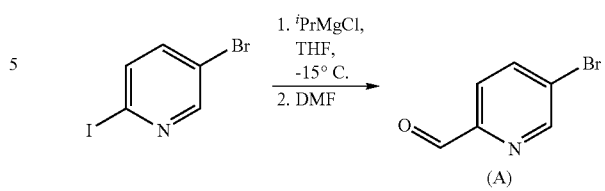

(A)

To a solution of 2-iodo-5-bromopyridine (18.4 g, 65 mmol) in THF (100 mL) at −15° C. was added isopropylmagnesium chloride (2M, 35 mL, 70 mmol) dropwise at a rate such that the temperature of the reaction did not exceed 0° C. The reaction was stirred at −15° C. for 1 h, then DMF (7.5 mL, 97 mmol) was added dropwise at a rate such that the temperature of the reaction did not exceed 0° C. The reaction was stirred for 30 min, then warmed to room temperature for an additional 1 h. The reaction was cooled back down to 0° C. and 2 N HCl (80 mL) was added dropwise, maintaining the temperature below 20° C. After stirring for 30 min, 2 N NaOH was added until pH 7 was reached. The organic layer was then separated and the aqueous layer extracted with $CH_2Cl_2$ (3×). The combined organic layers were dried over $MgSO_4$, concentrated and purified by flash chromatography ($SiO_2$, 10% EtOAc/hexanes) to furnish 5-bromopyridine-2-carbaldehyde (A) as a white solid (7.3 g, 60%). $^1H$ NMR (300 MHz, $CDCl_3$) δ 10.0 (s, 1H), 8.9 (s, 1H), 8.0 (d, 1H), 7.8 (d, 1H).

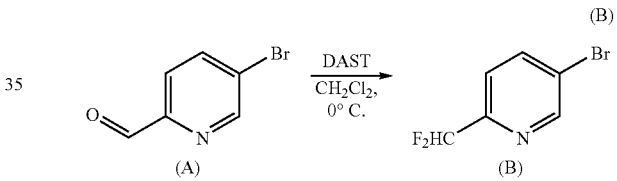

(B)

To a cooled solution of 5-bromopyridine-2-carbaldehyde (A) (7.0 g, 38 mmol) in $CH_2Cl_2$ (300 mL) at −78° C. was added diethylaminosulfur trifluoride (DAST, 10.8 mL, 83 mmol). The reaction was allowed to warm to room temperature over the course of 6 h, then it was quenched slowly with $H_2O$, washed with saturated aqueous $NaHCO_3$ and dried over $Na_2SO_4$. Concentration and purification by silica gel plug ($CH_2Cl_2$ eluent) furnished 5-bromo-2-difluoromethylpyridine (B) as brown crystals (5.3 g, 67%). $^1H$ NMR (300 MHz, $CDCl_3$) δ 8.8 (s, 1H), 8.0 (d, 1H), 7.6 (d, 1H), 6.6 (t, 1H).

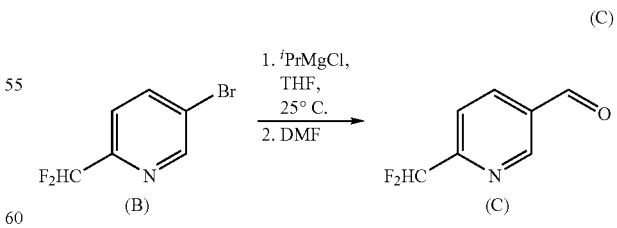

(C)

To a solution of 5-bromo-2-difluoromethylpyridine (B) (1.8 g, 8.6 mmol) in THF (40 mL) at 25° C. was added isopropylmagnesium chloride (2M, 8.6 mL, 17 mmol) dropwise. The reaction was allowed to stir for 2 h, then DMF (660 μL, 8.6 mmol) was added and the reaction was stirred for an additional 22 h. The reaction was quenched with 2M HCl and basified with 1M NaOH until pH 7 reached. The organic layer was separated and the aqueous layer was extracted with CH$_2$Cl$_2$. The combined organic layers were dried over Na$_2$SO$_4$, concentrated and purified by flash chromatography (10% EtOAc/hexanes) to furnish 6-difluoromethylpyridine-3-carbaldehyde (C) as an orange oil (320 mg, 24%).

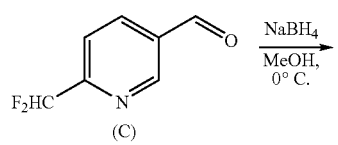

(C)    (D)

To a solution of 6-difluoromethylpyridine-3-carbaldehyde (C) (500 mg, 3.2 mmol) in MeOH (10 mL) at 0° C. was added NaBH$_4$ (60 mg, 1.6 mmol). The reaction was allowed to stir for 30 min, then 2M HCl was added until pH 2 was reached. The resulting solution was extracted with CH$_2$Cl$_2$ (3×) and the combined organic layers dried over Na$_2$SO$_4$ and concentrated to furnish (6-difluoromethyl-pyridin-3-yl)methanol (D) as an orange oil (420 mg, 82%) which was used in the next step without further purification. $^1$H NMR (300 MHz, CDCl$_3$) δ 8.6 (s, 1H), 7.9 (d, 1H), 7.6 (d, 1H), 6.6 (t, 1H), 4.8 (s, 2H).

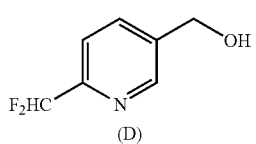

(D)    (E)

To a solution of (6-difluoromethylpyridin-3-yl)methanol (D) (450 mg, 2.8 mmol) in CH$_2$Cl$_2$ (10 mL) at room temperature was SOCl$_2$ (230 μL, 3.1 mmol). The reaction was allowed to stir for 1 h, then the reaction was quenched slowly with saturated aqueous NaHCO$_3$. The aqueous phase was extracted with CH$_2$Cl$_2$ (3×) and the combined organic layers were dried over Na$_2$SO$_4$ and concentrated to furnish the The resulting solution was extracted with CH$_2$Cl$_2$ (3×) and the combined organic layers dried over Na$_2$SO$_4$ and concentrated to furnish 5-chloromethyl-2-difluoromethylpyridine (E) as a reddish brown oil (490 mg, 98%) which was used in the next step without further purification. $^1$H NMR (300 MHz, CDCl$_3$) δ 8.7 (s, 1H), 7.9 (d, 1H), 7.6 (d, 1H), 6.6 (t, 1H), 4.6 (s, 2H).

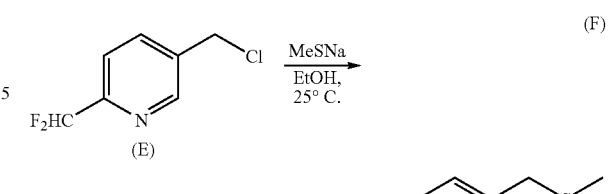

(E)    (F)

To a solution of sodium thiomethoxide (240 mg, 3.3 mmol) in EtOH (10 ml) at room temperature was added a solution of 5-chloromethyl-2-difluoromethylpyridine (E) (490 mg, 2.8 mmol) in EtOH (3 mL). The reaction was allowed to stir for 9 h, then the reaction was concentrated, taken up in Et$_2$O, and washed with H$_2$O. The organic phase was dried over Na$_2$SO$_4$ and concentrated to furnish 2-difluoromethyl-5-methylthiomethyl-pyridine (F) as an orange oil (422 mg, 81%) which was used in the next step without further purification. $^1$H NMR (300 MHz, CDCl$_3$) δ 8.6 (s, 1H), 7.8 (d, 1H), 7.6 (d, 1H), 6.6 (t, 1H), 3.7 (s, 2H), 2.0 (s, 3H).

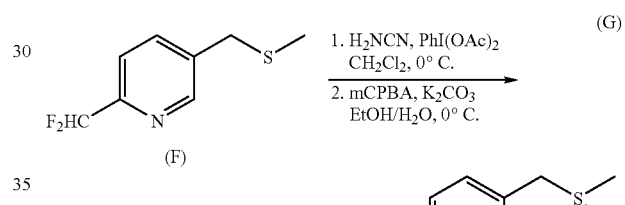

(F)

(7)

[(6-Difluoromethylpyridin-3-yl)methyl](methyl)-oxido-λ$^4$-sulfanylidenecyanamide (7) was synthesized from 2-difluoromethyl-5-methylthiomethylpyridine (F) in two steps as described in Examples I-B and I-C. Isolated as a white solid (51% yield). $^1$H NMR (300 MHz, CDCl$_3$) δ 8.7 (s, 1H), 8.0 (d, 1H), 7.8 (d, 1H), 6.7 (t, 1H), 4.7 (dd, 2H), 3.2 (s, 3H); LC-MS (ELSD): mass calcd for C$_9$H$_{10}$F$_2$N$_3$OS [M+H]$^+$, 246. Found 246.

Example VIII

Preparation of [1-(6-difluoromethylpyridin-3-yl)ethyl](methyl)-oxido-λ$^4$-sulfanylidenecyanamide (8)

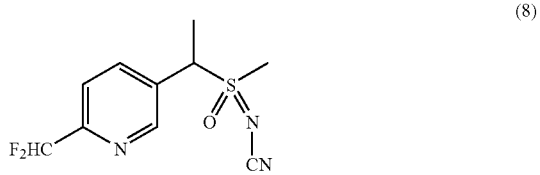

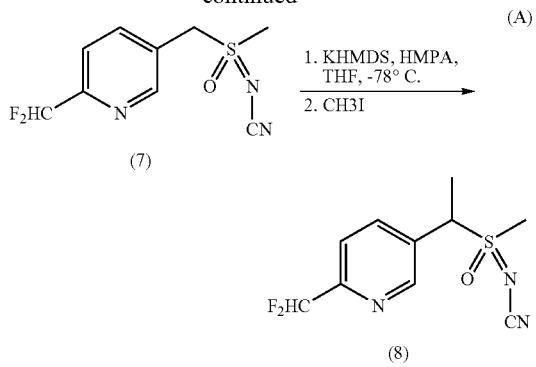

[1-(6-difluoromethylpyridin-3-yl)ethyl](methyl)-oxido-λ⁴-sulfanylidenecyanamide (8) was synthesized from [(6-difluoromethylpyridin-3-yl)methyl](methyl)-oxido-λ⁴-sulfanylidenecyanamide (7) in one step as described in Example II. Isolated as a colorless oil (74% yield) and a 1:1 mixture of diastereomers. $^1$H NMR (300 MHz, CDCl$_3$) δ (mixture of two diastereomers) 8.7 (s, 2H), 8.0 (d, 2H), 7.8 (d, 2H), 6.7 (t, 2H), 4.6 (q, 2H), 3.1 (s, 3H), 3.0 (s, 3H), 2.0 (d, 6H); LC-MS (ELSD): mass calcd for C$_{10}$H$_{12}$F$_2$N$_3$OS [M+H]$^+$, 260. Found 260.

Example IX

Preparation of [1-(6-pentafluoroethylpyridin-3-yl)ethyl](methyl)-oxido-λ⁴-sulfanylidenecyanamide (9)

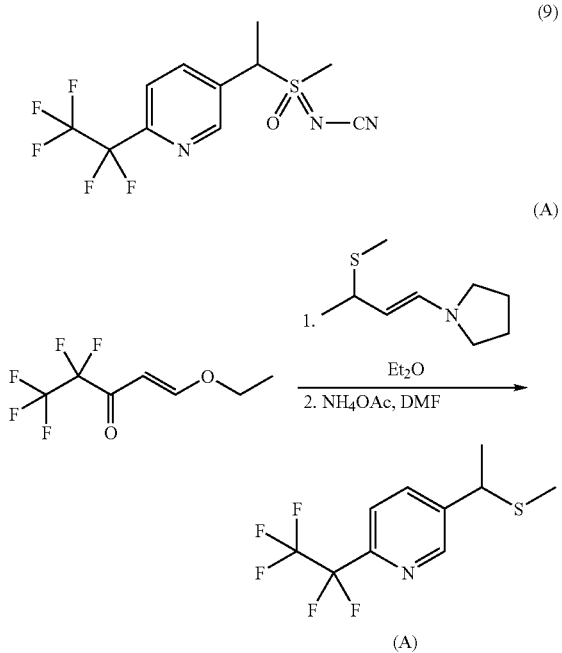

(E)-1-Ethoxy-4,4,5,5,5-pentafluoropent-1-en-3-one (1.09 g, 5 mmol) in anhydrous ethyl ether (5 mL) was treated with 1-((E)-3-methylthiobut-1-enyl)pyrrolidine (0.85 g, 5 mmol) in 2 mL dry ether at −15° C. over a period of 5 min and the reaction was continued for 20 min. Then the temperature was allowed to rise to room temperature and the reaction continued for 3 h. The solvent was removed under reduced pressure and the residue re-dissolved in anhydrous DMF (5 mL). Ammonium acetate (0.58 g, 7.5 mmol) was added and the mixture stirred at room temperature over a weekend. Water was added and mixture extracted with ether three times. The combined organic layer was washed with brine, dried over anhydrous Na$_2$SO$_4$, filtered, concentrated, and purified on silica gel eluted with 8% EtOAc in hexane (v/v) to give 0.16 g of the desired 5-(1-methylthioethyl)-2-pentafluoroethylpyridine (A) as brownish colored oil in 12% yield. GC-MS: mass calcd for C$_{10}$H$_{11}$F$_2$N$_3$S [M]$^+$ 271. Found 271.

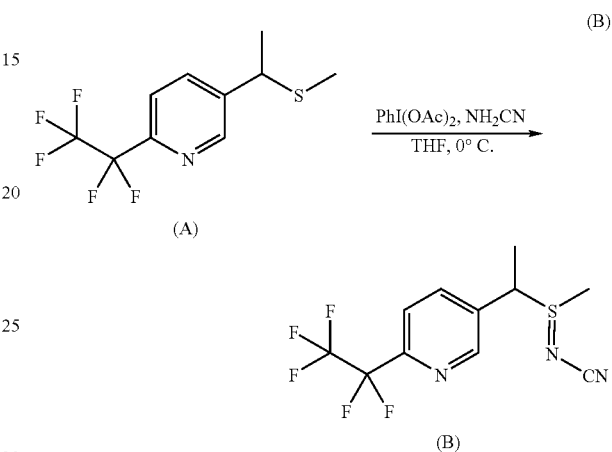

To a stirred solution of the 5-(1-methylthioethyl)-2-pentafluoro-ethylpyridine (A) (0.16 g, 0.6 mmol) and cyanamide (0.025 g, 0.6 mmol) in THF (3 mL) cooled to 0° C. was added iodobenzene diacetate (0.19 g, 0.6 mmol) in one portion and the resulting mixture was stirred at 0° C. for 2 h and then at room temperature overnight. The solvent was removed in vacuo and the resulting mixture was suspended in brine-saturated NaHCO$_3$ (9:1), which was then extracted with CH$_2$Cl$_2$-EtOAc (1:1, v/v) two times. The combined organic layer was dried over Na$_2$SO$_4$, filtered, concentrated, and dried to give 0.16 g of (1-[6-[pentafluoroethyl]pyridin-3-yl]ethyl)(methyl)-λ⁴-sulfanylidenecyanamide (B) as a brownish oil in 85% yield. LC-MS: mass calcd for C$_{11}$H$_{10}$F$_5$N$_3$S [M]$^+$ 311.28. Found [M−1]$^+$ 309.84

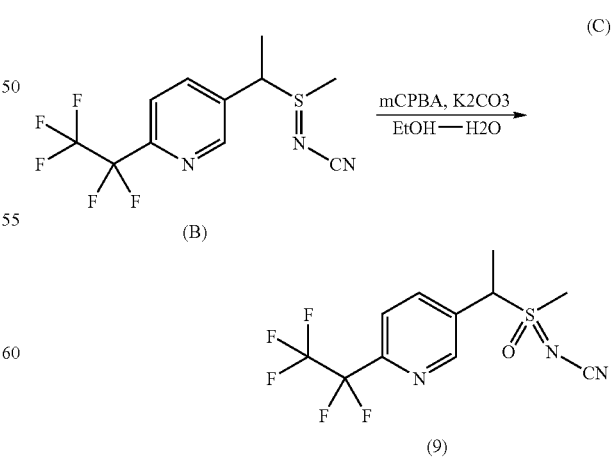

To a stirred solution of the 80% 3-chloroperoxybenzoic acid (0.17 g, ca 0.8 mmol) in ethanol (3 mL) cooled to 0° C.

was added 20% aqueous potassium carbonate (1.0 mL, 1.5 mmol and the resulting mixture was stirred at 0° C. for 20 min. Then (1-{6-[pentafluoroethyl]pyridin-3-yl}ethyl)(methyl)-λ$^4$-sulfanylidenecyanamide (B) was added at once and the mixture was stirred at 0° C. for 1 h. The reaction was quenched with a small spatula of solid sodium thiosulfate. Most of the solvent was evaporated and brine solution was added and the mixture extracted with CH$_2$Cl$_2$ three times. The combined organic layer was dried over Na$_2$SO$_4$, filtered and concentrated and the residue was purified on silica gel using 10% acetone in CH$_2$Cl$_2$ (v/v) to give 0.089 g of [1-(6-pentafluoroethylpyridin-3-yl)ethyl](methyl)-oxido-λ$^4$-sulfanylidenecyanamide (9) as a white solid in 54% yield. LC-MS: mass calcd for C$_{10}$H$_{10}$F$_5$N$_3$OS [M]$^+$ 327.28. Found [M−1]$^+$ 325.83.

Example X

Preparation of 2-[(6-trifluoromethylpyridin-3-yl) methyl]-1-oxidotetrahydro-1H-λ$^4$-thien-1-ylidenecyanamide (10)

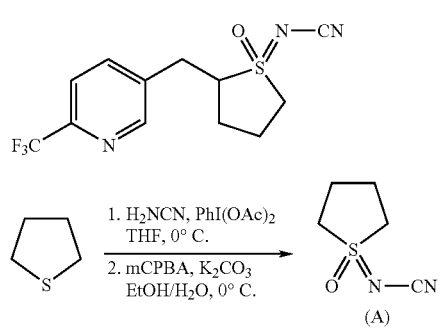

1-Oxidotetrahydro-1H-λ$^4$-thien-1-ylidenecyanamide (A) was prepared from tetrahydrothiophene by a two step procedure as described in Examples VI-A and VI-B (69% yield). $^1$H NMR (300 MHz, CDCl$_3$) δ 3.5 (m, 2H), 3.3 (m, 2H), 2.3-2.5 (m, 4H); GC-MS: mass calcd for C$_5$H$_8$N$_2$OS [M+H]$^+$, 144. Found 144.

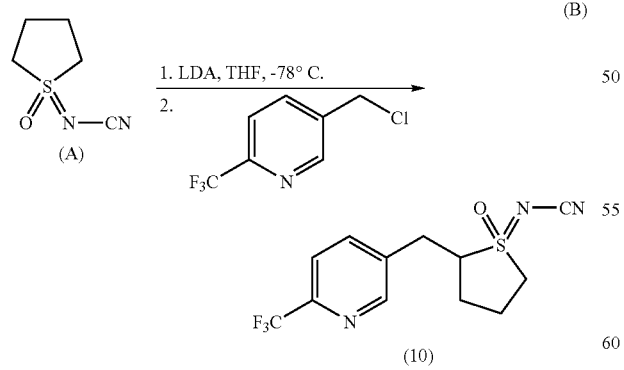

To a solution of 1-oxidotetrahydro-1H-λ$^4$-thien-1-ylidenecyanamide (A) (200 mg, 1.4 mmol) in THF (10 ml) at −78° C. was added LDA solution in THF (1.8M, 850 μL, 1.5 mmol). The reaction was allowed to stir for 45 min, then 5-chloromethyl-2-trifluoromethylpyridine (300 mg, 1.5 mmol) was added dropwise. The solution was allowed to stir at −78° C. for 1 h, then it was warmed to 0° C. for an additional 2 h. The reaction was then quenched with saturated aqueous NH$_4$Cl and extracted with CH$_2$Cl$_2$. The combined organic layers were dried over Na$_2$SO$_4$, concentrated, and purified by flash chromatography to furnish 2-[(6-trifluoromethylpyridin-3-yl)methyl]-1-oxidotetrahydro-1H-λ$^4$-thien-1-ylidenecyanamide (10) as a yellow oil (41 mg, 9%). IR (film) 2946, 2194, 1339 cm$^{-1}$; $^1$H NMR (300 MHz, CDCl$_3$) δ (mixture of two diastereomers) 8.6 (s, 2H), 7.8 (m, 2H), 7.7 (d, 1H), 7.6 (d, 1H), 3.4-3.8 (m, 7H), 3.3 (m, 1H), 3.0-3.2 (m, 2H), 1.9-2.6 (m, 8H); LC-MS (ELSD): mass calcd for C$_{12}$H$_{13}$F$_3$N$_3$OS [M+H]$^+$, 304. Found 304.

Example XI

Preparation of 2-trifluoromethyl-5-(1{methyl(oxido) [oxido(oxo)hydrazono]-λ$^4$-sulfanyl}ethyl)pyridine (11)

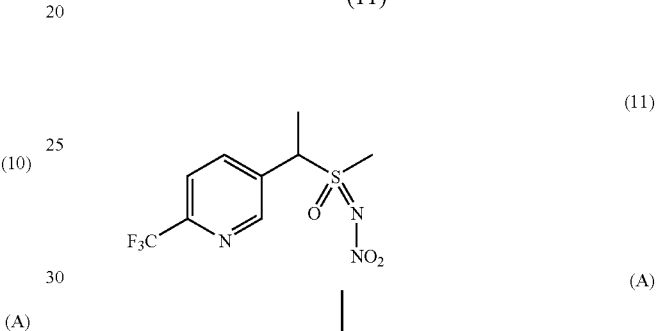

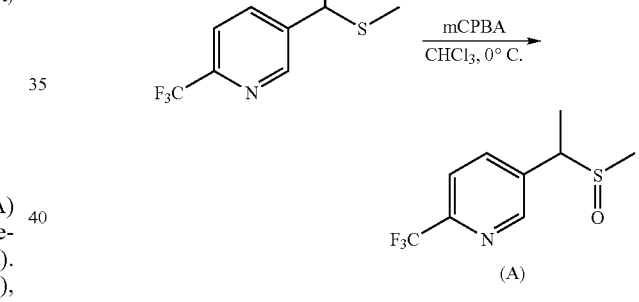

To a solution of 5-(1-methylthioethyl)-2-trifluoromethylpyridine (2.0 g, 9 mmol) in CHCl$_3$ (20 mL) at 0° C. was added solution of mCPBA (2.1 g, 10 mmol) in CHCl$_3$ (25 mL) over the course of 1.5 h. The solution was stirred an additional 2 h, then it was concentrated and purified by flash chromatography (10% MeOH/CH$_2$Cl$_2$) to furnish 5-(1-methylsulfinylethyl)-2-trifluoromethylpyridine (A) as a yellow oil (710 mg, 33%) and a ~2:1 mixture of diastereomers. $^1$H NMR (300 MHz, CDCl$_3$) δ (major diastereomer) 8.7 (s, 1H), 7.8 (d, 1H), 7.7 (d, 1H), 4.0 (q, 1H), 2.4 (s, 3H), 1.75 (d, 3H); (minor diastereomer) 8.6 (s, 1H), 7.9 (d, 1H), 7.7 (d, 1H), 3.8 (q, 1H), 2.3 (s, 3H), 1.8 (d, 3H); LC-MS (ELSD): mass calcd for C$_9$H$_{11}$F$_3$NOS [M+H]$^+$, 238. Found 238.

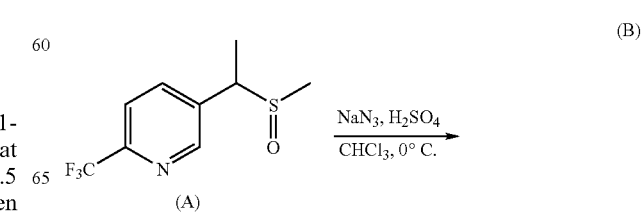

-continued

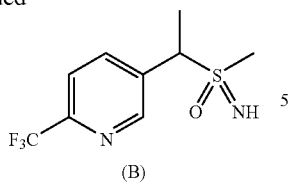
(B)

To a solution of 5-(1-methylsulfinylethyl)-2-trifluoromethylpyridine (A) (600 mg, 2.5 mmol) in CHCl$_3$ (5 mL) at 0° C. was added sodium azide (260 mg, 4.0 mmol) and H$_2$SO$_4$ (1 mL). The reaction was warmed to 55° C. until gas evolution was observed, then it was cooled back down to room temperature overnight. The liquid was decanted into a separate flask and the residual syrup was dissolved in H$_2$O, basified with Na$_2$CO$_3$ and extracted with CH$_2$Cl$_2$. The combined organic layers were dried over Na$_2$SO$_4$, concentrated and purified by flash chromatography to furnish 5-[1-(methylsulfonimidoyl)ethyl]-2-trifluoromethylpyridine (B) as a yellow oil (130 mg, 20%) and a ~1:1 mixture of diastereomers. $^1$H NMR (300 MHz, CDCl$_3$) δ (mixture of diastereomer) 8.8 (d, 2H), 8.0 (dd, 2H), 7.8 (d, 2H), 4.4 (m, 2H), 2.9 (s, 3H), 2.85 (s, 3H), 1.8 (m, 6H); LC-MS (ELSD): mass calcd for C$_9$H$_{11}$F$_3$N$_2$OS [M]$^+$, 252. Found 252.

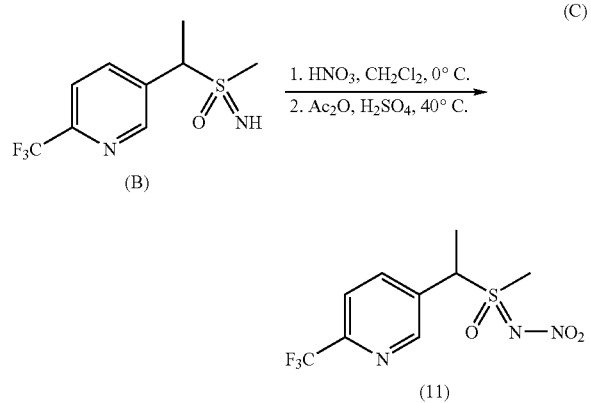

To a solution of 5-[1-(methylsulfonimidoyl)ethyl]-2-trifluoromethylpyridine (B) (100 mg, 0.4 mmol) in CH$_2$Cl$_2$ (2 mL) at 0° C. was added HNO$_3$ (16 μL, 0.4 mmol) dropwise. To the resulting suspension was added acetic anhydride (750 μL) and concentrated H$_2$SO$_4$ (5 μL) and the mixture was heated to 40° C. The suspension slowly became homogeneous over the course of 15 min. The solvent was then removed and the crude residue was dissolved in H$_2$O. Solid Na$_2$CO$_3$ was added until pH 8 was reached and the aqueous phase was extracted with CH$_2$Cl$_2$. The combined organic layers were dried over Na$_2$SO$_4$, concentrated and purified by flash chromatography to furnish 2-trifluoromethyl-5-(1-{methyl(oxido)-[oxido(oxo)hydrazono]-λ$^4$-sulfanyl}ethyl)pyridine (11) as a yellow oil (22 mg, 19%) and a 1:1 mixture of diastereomers. $^1$H NMR (300 MHz, CDCl$_3$) δ (mixture of diastereomers) 8.8 (d, 2H), 8.1 (m, 2H), 7.8 (m, 2H), 5.1 (q, 1H), 5.0 (q, 1H), 3.3 (s, 3H), 3.25 (s, 3H), 2.0 (m, 6H); LC-MS (ELSD): mass calcd for C$_9$H$_{11}$F$_3$N$_3$O$_3$S [M+H]$^+$, 298. Found 298.

Example XII

Preparation of [6-(1,1-difluoroethyl)pyridin-3-yl)ethyl](methyl)-oxido-λ4-sulfanylidenecyanamide (12)

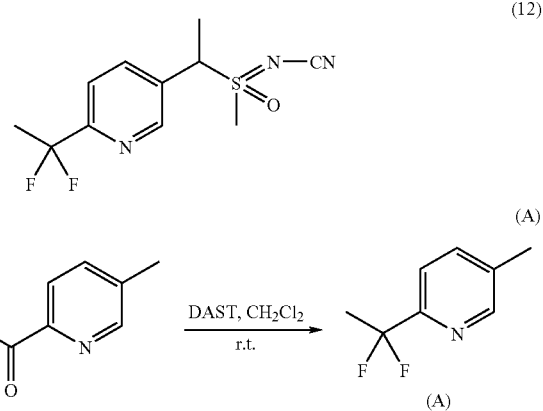

To a solution 5-methyl-2-acetylpyridine (9.9 g, 73.3 mmol) in molecule sieves-dried CH$_2$Cl$_2$ (150 mL) was added diethylamino sulfolnyltrifluoride (DAST) (25.8 g, 260 mmol) at room temperature and the mixture was stirred at room temperature overnight. More DAST (12 g, 74 mmol) was added and the reaction continued for two more days after which an additional DAST (3.8 g, 23 mmol) was added and the reaction continued for another 3 days. After the reaction was quenched slowly with saturated NaHCO$_3$ at 0° C., the organic phase was separated, dried over Na$_2$SO$_4$, filtered, and concentrated. The residue was purified on silica gel eluted with 8% EtOAc in hexane to give 3.91 g of 2-(1,1-difluoroethyl)-5-methylpyridine (A) as a light brownish oil in 34% yield. GC-MS: mass calcd for C$_8$H$_9$F$_2$N [M]$^+$ 157. Found 157.

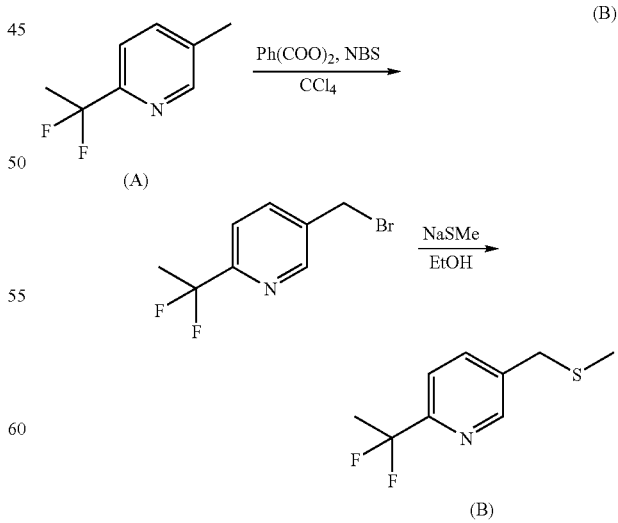

A mixture of 2-(1,1-difluoroethyl)-5-methylpyridine (A) (2.0 g, 12.7 mmol), N-bromosuccinimide (2.2 g, 12.7 mmol)

and benzoylperoxide (0.15 g, 0.63 mmol) in carbon tetrachloride (100 mL) was refluxed overnight. After the solid was removed by filtration, the filtrate was concentrated. The residue was re-dissolved in ethanol (40 mL) and sodium thiomethoxide (1.33 g, 19 mmol) was added at room temperature and stirred for 3 h. The solvent was removed under reduced pressure and the remaining mixture was dissolved in $CH_2Cl_2$ and water. After separation, the organic layer was dried over $Na_2SO_4$, filtered and concentrated. The crude product 2-(1,1-difluoroethyl)-5-methylthiomethyl-pyridine (B) was 94% pure on GC/MS, which was used directly for the next reaction without further purification. GC-MS: mass calcd for $C_9H_{11}F_2NS$ $[M]^+$ 203. Found 203.

$\lambda^4$-sulfanylidenecyanamide (C) (0.72 g, 2.96 mmol) dissolved in 5 mL of $CH_2Cl_2$ was added dropwise over a period of 30 min. The mixture was stirred rapidly at room temperature for 1.5 h and then filtered through a filtering paper to remove some insolubles. The mixture was then separated in separation funnel after ethyl acetate was added to facilitate the separation. The aqueous phase was extracted with $CH_2Cl_2$ twice. The combined organics was washed with brine, dried over dry $Na_2SO_4$, filtered, concentrated, and briefly purified on silica gel with 70% acetone in hexane to give 0.652 g of the desired product [(6-(1,1-difluoroethylpyridin-3-yl)methyl](methyl)-oxido $\lambda^4$-sulfanylidenecyanamide (D) as a white solid in 87% yield. LC-MS: mass calcd for $C_{10}H_{11}F_2N_3OS$ $[M]^+$ 259.28. Found $[M+1]^+$ 260.02.

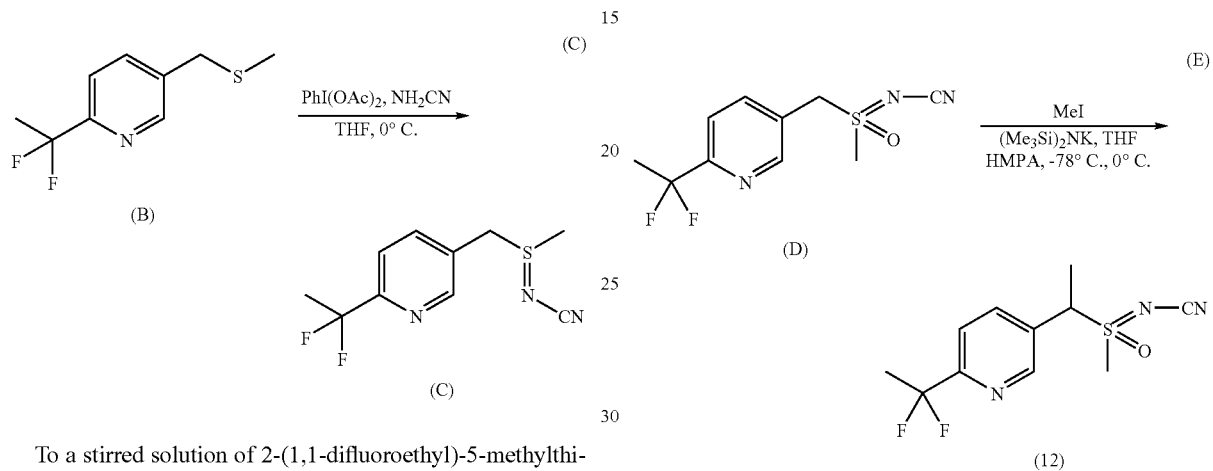

To a stirred solution of 2-(1,1-difluoroethyl)-5-methylthiomethylpyridine (B) (1.22 g, 6.0 mmol) and cyanamide (0.25 g, 6.0 mmol) in THF (7 mL) cooled to 0° C. was added iodobenzene diacetate (1.93 g, 6.0 mmol) in one portion and the resulting mixture was stirred at 0° C. for 1 h and then at room temperature for 2 h. The solvent was removed in vacuo and the resulting mixture was purified on silica gel using 60% acetone in hexane (v/v) to give 1.22 g of [(6-(1,1-difluoroethylpyridin-3-yl)methyl](methyl)-$\lambda^4$-sulfanylidenecyanamide (C) (84% yield) as brownish oil which turned into a brownish solid after standing in the refrigerator overnight. LC-MS: mass calcd for $C_{10}H_{11}F_2N_3S$ $[M]^+$ 243.28. Found $[M+1]^+$ 244.11.

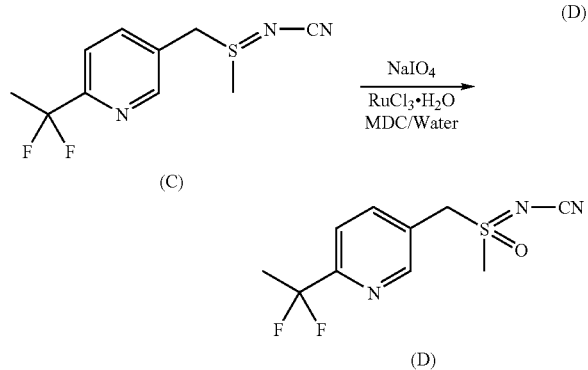

To a 100 ml round bottom flask equipped with magnetic stirrer, addition funnel, and thermometer was charged the sodium periodate (0.95 g, 4.44 mmol) and water (12 mL). After the solid had dissolved, 15 mL of $CH_2Cl_2$ was added followed by the ruthenium trichloride hydrate (0.033 g, 0.15 mmol). [6-(1,1-difluoroethylpyridin-3-yl)methyl](methyl)-

To a solution of [(6-(1,1-difluoroethylpyridin-3-yl)methyl](methyl)-oxido $\lambda^4$-sulfanylidenecyanamide (D) (0.55 g, 2.0 mmol) and HMPA (0.09 mL, 0.55 mmol) in 20 mL anhydrous THF was added 0.5 M potassium bis(trimethylsilyl) amide in toluene (4.4 mL, 2.2 mmol) at −78° C. dropwise. After 45 min, iodomethane (0.14 mL, 2.2 mmol) was added in one portion via a syringe. Ten minutes later, the temperature was allowed to rise to 0° C. and mixture continued to stir for 1.5 h. The reaction was quenched with saturated aqueous $NH_4Cl$, diluted with brine, extracted once each with EtOAc and $CH_2Cl_2$. The combined organic layer was dried over $Na_2SO_4$, filtered, and concentrated. The residue was purified by preparative HPLC to give 0.15 g of the desired [6-(1,1-difluoroethyl)pyridin-3-yl)ethyl](methyl)-oxido-$\lambda^4$-sulfanylidenecyanamide (12) in 26% yield. LC-MS: mass calcd for $C_{11}H_{13}F_2N_3OS$ $[M]^+$ 273.31. Found $[M+1]^+$ 274.21.

Examples XIII-XXI

Insecticidal Testings

The compounds identified in the foregoing examples were tested against cotton aphid, green peach aphid, sweet potato whitefly, brown planthopper, green leafhopper, termite, cat flea and/or brown dog tick using procedures described hereinafter.

Example XIII

Insecticidal Test for Cotton Aphid (*Aphis gossypii*) in Foliar Spray Assay

Squash with fully expanded cotyledon leaves were trimmed to one cotyledon per plant and infested with cotton aphid (wingless adult and nymph) 1 day prior to chemical application. Each plant was examined before chemical application to ensure proper infestation (ca. 30-70 aphids per plant). Compounds (2 mg) were dissolved in 2 ml of acetone: methanol (1:1) solvent, forming stock solutions of 1000 ppm. The stock solutions were then diluted with a diluent consisting 80 parts of 0.025% Tween 20 in H$_2$O and 20 parts of acetone:methanol (1:1). A hand-held Devilbiss sprayer was used to apply the test solutions until runoff to both sides of the squash cotyledon leaves. Four plants (4 replications) were used for each concentration of each compound. Reference plants (solvent check) were sprayed with the diluent only. Treated plants were held in a holding room for 3 days at approximately 23° C. and 40% RH before the number of live aphids on each plant was recorded. Insecticidal activity was measured by Corrected % Control using Abbott's correction formula and presented in Table 1:

Corrected % Control=100*(X−Y)/X where X=No. of live aphids on solvent check plants
Y=No. of live aphids on treated plants

TABLE 1

| % Control of cotton aphid on squash (foliar spray) | | | | |
|---|---|---|---|---|
| Cmpd # | 0.049 ppm | 0.195 ppm | 0.781 ppm | 3.13 ppm |
| 1 | A | A | A | A |
| 2 | A | A | A | A |
| 3 | A | A | A | A |
| 4 | A | A | A | A |
| 5 | E | B | A | A |
| 6 | H | H | B | B |
| 7 | F | B | A | A |
| 8 | C | A | A | A |
| 9 | H | H | E | A |
| 10 | H | H | D | C |
| 11 | D | D | A | A |
| 12 | H | H | A | A |

In each case of Table 1 the rating scale is as follows:

| % Control (or Mortality) | Rating |
|---|---|
| 90-100 | A |
| 80-89 | B |
| 70-79 | C |
| 60-69 | D |
| 50-59 | E |
| Less than 50 | F |
| Inactive | G |
| Not tested | H |

The compounds that showed high activities against cotton aphid in Table 1 were selected for further testing against green peach aphid using procedures described hereinafter.

Example XIV

Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) 2-3 days prior to chemical application. Four seedlings were used for each treatment. Compounds (2 mg) were dissolved in 2 ml of acetone:methanol (1:1) solvent, forming stock solutions of 1000 ppm. The stock solutions were then diluted with a diluent consisting 80 parts of 0.025% Tween 20 in H$_2$O and 20 parts of acetone:methanol (1:1). A hand-held Devilbiss sprayer was used for spraying the test solutions to both sides of cabbage leaves until runoff. Reference plants (solvent check) were sprayed with the diluent only. Treated plants were held in a holding room for three days at approximately 23° C. and 40% RH prior to grading. Evaluation was conducted by counting the number of live aphids per plant under a microscope. Insecticidal activity was measured by using Abbott's correction formula:

Corrected % Control=100*(X−Y)/X where X=No. of live aphids on solvent check plants
Y=No. of live aphids on treated plants
The Corrected % Control values from assays are given in Table 2.

TABLE 2

| Activity against green peach aphid on cabbage | | | |
|---|---|---|---|
| | % Control at ppm, foliar spray | | |
| Cmpd # | 0.195 ppm | 0.781 ppm | 3.125 ppm |
| 1 | G | F | A |
| 2 | B | A | A |
| 3 | F | F | D |
| 4 | B | A | A |
| 5 | G | F | B |
| 8 | F | F | F |
| 11 | C | B | A |
| 12 | H | E | B |

In each case of Table 2 the rating scale is the same as that used for Table 1.

The compounds that showed high activities against green peach aphid in Table 2 were selected for further testing against brown planthopper and green leafhopper using procedures described hereinafter.

Example XV

Insecticidal Test for Brown Planthopper (*Nilaparvata lugens*) and Green Leafhopper (*Nephotettix* Sp.)

A foliar spray assay and a root-uptake systemic assay were performed on both brown planthopper and green leafhopper. Four-week-old rice seedlings were submerged in 3-cm depth of water in the bottom portion (high 5 cm, diameter 3 cm) of a 2-part glass cylinder (high 18 cm, diameter 3 cm). A metal screen was used to hold the seedlings within the bottom portion. Scotch tape was used to bind the two portions of the cylinder after setting up the seedlings. A metal cap was used to cover the cylinder. There were 4 cylinders for each treatment. The test compound was dissolved in acetone to make a 10,000 ppm stock solution. For the foliar spray assay, this stock solution was diluted with water to make 10, 2.5, 0.31, 0.08 and 0.02 ppm test solutions. A volume of 0.5 ml of a test solution or solvent blank as check was sprayed into the glass cylinder. For systemic test, the stock solution was incorporated at final test concentrations of 10, 2.5, 0.31, 0.08 and 0.02 ppm in the water in which rice seedlings were submerged. In both foliar spray and systemic tests, five laboratory-reared 3$^{rd}$ instar nymphs of brown planthopper or green leafhopper were introduced into each cylinder 3 hr after insecticide application. The treated test units were kept in a growth chamber with conditions set as followings: Temperature 28±0.5° C.; Relative humidity 70±0.5%; Photoperiod 14 hr light:8 hr dark.

Mortality of hoppers was observed at 2 and 6 days after infestation. The corrected % Control values relative to mortality in the solvent reference are given in Tables 3 and 4.

TABLE 3

Foliar spray activity against brown planthopper and green leafhopper on rice.

| | % Control at ppm against green leafhopper | | | | | % Control at ppm against brown planthopper | | | | |
|---|---|---|---|---|---|---|---|---|---|---|
| Comp # | 0.02 | 0.08 | 0.31 | 2.5 | 10 | 0.02 | 0.08 | 0.31 | 2.5 | 10 |
| 2 | D | A | A | A | A | F | E | A | A | A |
| 4 | E | B | A | A | A | F | E | B | A | A |

TABLE 4

Systemic activity against brown planthopper and green leafhopper on rice.

| | % Control at ppm against green leafhopper | | | | | % Control at ppm against brown planthopper | | | | |
|---|---|---|---|---|---|---|---|---|---|---|
| Comp # | 0.02 | 0.08 | 0.31 | 2.5 | 10 | 0.02 | 0.08 | 0.31 | 2.5 | 10 |
| 2 | D | B | A | A | A | F | C | A | A | A |
| 4 | E | C | A | A | A | F | E | A | A | A |

In each case of Tables 3 and 4 the rating scale is the same as that used for Table 1.

Compound 2 was selected for advanced testing against sweet potato whitefly, green peach aphid, termite, cat flea and brown dog tick using procedures described hereinafter.

Example XVI

Insecticidal Test for Sweet Potato Whitefly (*Bemisia tabaci*) in Foliar Spray Assay This test was designed to measure the capability of whitefly eggs and/or young nymphs to develop to large nymphs. Cotton seedlings at the growth stage of one or two expanding true leaf were trimmed so that only the first true leaf remained (cotyledon leaves were also removed). The plants were pre-infested with sweet potato whitefly eggs by keeping plants next to the colony-keeping plants for two days. The infested plants were carefully checked for presence of similar egg density before use in the insecticidal tests. Master solutions of test compounds at 1000 ppm were prepared in acetone:methanol(1:1). The 12.5 ppm spray solutions were then made by diluting 0.188 mL of the master solution with 14.812 ml of 0.025% Tween 20 in water. The lower concentrations were made by diluting the 12.5 ppm spray solution with a diluent consisting 98.75 parts of 0.025% Tween 20 in water and 1.25 parts of acetone:methanol (1:1). The diluent was used as solvent control. The test solutions were sprayed with a hand-held Devilbiss sprayer until runoff to both sides of the infested cotton leaves. Four plants (4 replications) were used for each treatment. Treated plants were held in a holding room for 12 days at approximately 23° C. and 40% RH before evaluation. To evaluate the efficacy of the compounds, the number of live large nymphs in an area of 1 square inch on the lower surface of the treated cotton leaves was counted under a microscope. Insecticidal activity was determined by Corrected % Control using Abbott's correction formula and presented in Table 5:

Corrected % Control=$100*(X-Y)/X$ where X=No. of live large nymphs on solvent check plants
Y=No. of live large nymphs on treated plants

TABLE 5

Activity against sweet potato whitefly on cotton

| | % Control at ppm, foliar spray | | |
|---|---|---|---|
| Comp # | 0.781 ppm | 3.125 ppm | 12.500 ppm |
| 2 | 80 | 94 | 100 |

Example XVII

Insecticidal Test For Green Peach Aphid (*Myzus Persicae*) in Root Uptake Assay

Systemic activity of compound 2 against green peach aphid was evaluated in a root uptake assay. Bell peppers (*Capsicum annum* var. California Wonder) was used as test plant seeded and grown in rock wool plugs. Plants were grown to expanding $1^{st}$ true leaf stage. The rock wool plugs containing individual plants were placed in 1-ounce cups and surrounded with white clean sand. Five plants were used for each treatment. Stock solution of 1000 ppm was made by dissolving 2 mg of technical test compound in 2 mL acetone. The highest test concentration (10 ppm, 0.05 mg/5 ml) was prepared by diluting 0.32 mL stock solution with 1.6 mL acetone and 30.08 mL DI water, containing 6% acetone. Lower test concentrations were prepared by sequentially diluting 6.5 mL higher concentration (start from the 10 ppm test solution) with 26.0 ml acetone:DI water (6:94). A volume of 5 mL was applied to each cup (each plant). Use 6% acetone in water as solvent check. After insecticide application, the seedlings were infested with green peach aphids and held in a growth chamber (25° C., 50% R.H, 16 hr light: 8 hr drak). Number of live aphid on each plant was counted at 3 days after infestation. Calculations for % control were based on a corrected basis compared to the populations on the solvent check plants.

Corrected % Control=$100*(X-Y)/X$ where X=No. of live aphids on solvent check plants
Y=No. of live aphids on treated plants The Corrected % Control values from lower test rates are given in Table 6.

TABLE 6

Systemic activity against green peach aphid on pepper

| | % Control, root uptake systemic | | | |
|---|---|---|---|---|
| Comp # | 0.08 ug/plant | 0.4 ug/plant | 2 ug/plant | 10 ug/plant |
| 2 | 61 | 95 | 100 | 100 |

Example XVIII

Insecticidal Test for Cotton Aphid (*Aphis gossypii*) in Seed Coating Assay

Compound 2 was tested in an assay designed to evaluate its systemic activity for control of cotton aphid through seed-coating prior to planting. The crop used in this assay was a hybrid squash (var. Pic-N-Pic). Test compound was formulated in a 10% SC formulation. For the 1 mg/seed treatment, the original 10% formulation was used. For the 0.1 mg/seed treatment, the 10% formulation were diluted 10× with DI water before application. Ten squash seeds were used for each treatment. Seeds were placed on waxed paper and a pipette was used to apply the original or diluted formulations to each seed. One half (5 ul) of the sample was spread onto one side of a seed. Once dried (approximately 1 hr), the seed was flipped over and the 2nd half of sample was spread over the other side. The air-dried, treated seeds were individually planted into 3 inch pots containing metro mix. The pots were placed on a California cart and moved into the greenhouse for sub watering only. Thirteen days later, when the seedlings were approximately 9 inch tall with three expanding true leaves, the 1st leaf was infested with approximately 40 wingless aphids. The infested plants were kept in an environmental holding room (23 C, 40% RH, 16 hr light: 8 hr dark) for three days before the number of live aphids was counted under a microscope. Calculations for % control were based on a corrected basis compared to the populations on the reference plants germinated from seeds treated with the formulation blank.

Corrected % Control=100*(X−Y)/X where X=No. of live aphids on reference plants

Y=No. of live aphids on treated plants

The Corrected % Control values from assays are given in Table 7.

TABLE 7

Systemic activity against cotton aphid on squash

| Comp # | % Control, root uptake systemic | |
|---|---|---|
| | 0.1 mg/seed | 1 mg/seed |
| 2 | 99.7 | 100 |

Example XIX

Insecticidal Test for Eastern Subterranean Termite (*Reticulitermes Flavipes*) in Filter Paper Assay Activity of Compound 2 was evaluated for its activity on Eastern subterranean termite. Technical material of the test compound was formulated in acetone on a wt/wt basis to deliver 1000, 500, 200, 50, 12.5, 3.12 and 0.78 ppm to 42.5 mm Whatman No. 1 filter papers per 200 ul of pipetted solution. Each test concentration was applied to six filter papers (6 reps). Six acetone-only control units and six DI water-only control units were also prepared. The filter papers were dried overnight in the fume hood before they were placed into 60×15 mm Fisher Brand plastic Petri dishes. A volume of 200 ul DI water was pipetted onto each filter paper at the time of test set-up, just prior to infesting with termites. Ten worker termites were added to each Petri dish and covered. The infested Petri dishes were put in the laboratory Conviron at 28° C. and 60% RH. Termite mortality was recorded at 1, 2, 4, 7, and 10 days after infestation (DAI). Throughout the duration of the test, an average of 150 ul of DI water was added daily to the filter papers to retain moisture. Results are presented in Table 8.

TABLE 8

Activity against Eastern subterranean termite.

| Comp # | Conc. | % Termite mortality | | | | |
|---|---|---|---|---|---|---|
| | | 1 DAI | 2 DAI | 4 DAI | 7 DAI | 10 DAI |
| 2 | 0.78 ppm | 7 | 17 | 58 | 73 | 80 |
| | 3.13 ppm | 25 | 48 | 67 | 83 | 87 |
| | 12.5 ppm | 48 | 67 | 90 | 100 | 100 |
| | 50 ppm | 55 | 72 | 98 | 100 | 100 |
| | 200 ppm | 55 | 72 | 80 | 100 | 100 |
| | 500 ppm | 63 | 82 | 98 | 100 | 100 |
| | 1000 ppm | 87 | 90 | 100 | 100 | 100 |
| Acetone Control | — | 0 | 0 | 0 | 2 | 3 |
| DI Water Control | — | 7 | 7 | 7 | 7 | 7 |

Example XX

Insecticidal Test for Cat Flea (*Ctenocephalides felis*) in Filter Wool Assay

Compound 2 was evaluated in a dose response series to establish the range of activity of the test compound. Technical material was dissolved in acetone and diluted with the same solvent to obtain the test concentrations. Bioassays were conducted by treating polyester aquarium filter wool with 1.0 ml of the test solution, thoroughly saturating the substrate and allowing it to dry for at least 1 hour. The dry filter wool was then placed into 10 cm plastic Petri dishes and covered with the lid. Each treatment was replicated 5 times. Approximately 15 unfed cat flea adults were placed into each replicate of each dosage being evaluated. Mortality was assessed at 2, 8, 24 and 48 hours after introduction of the fleas into the test system. The mean percent mortality for each dosage group and time interval was determined and results from the 48-hour observation are presented in Table 9.

TABLE 9

Activity against cat flea.

| Comp # | Conc. | % Flea mortality |
|---|---|---|
| 2 | 5 ppm | 18 |
| | 50 ppm | 25 |
| | 500 ppm | 40 |
| | 5,000 ppm | 57 |

Example XXI

Insecticidal Test for Brown Dog Tick (*Rhipicephalus sanguineus*) in Glass Plate Assay Compound 2 was evaluated in a dose response series to establish the range of activity of the test compound. Technical material was dissolved in acetone and diluted with the same solvent to obtain the test concentrations. Tick bioassays were conducted by applying 1.0 ml of the test substance to clean dry glass plates confined by 10 cm grease pencil circles drawn on the plates and spread evenly with an acid brush. The plates were allowed to dry for at least 1 hour before adult ticks were confined to the treated substrate using 10 cm Petri dish lids. Each treatment was replicated 5 times. Approximately 5 adult ticks were placed into each replicate. Mortality was assessed at 2, 8, 24 and 48 hours after introduction of the ticks into the test system. The mean percent mortality for each dosage group and time interval was determined and results from the 48-hour observation are presented in Table 10.

TABLE 10

Activity against brown dog tick.

| Comp # | Conc., ppm | % Tick mortality |
|---|---|---|
| 2 | 50 ppm | 28 |
|   | 500 ppm | 61 |

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta*, *Trichoplusia ni*, *Anticarsia gemmatalis*, *Rachiplusia nu*, *Plutella xylostella*, *Chilo* spp., *Scirpophaga incertulas*, *Sesamia inferens*, *Cnaphalocrocis medinalis*, *Ostrinia nubilalis*, *Cydia pomonella*, *Carposina niponensis*, *Adoxophyes orana*, *Archips argyrospilus*, *Pandemis heparana*, *Epinotia aporema*, *Eupoecilia ambiguella*, *Lobesia botrana*, *Polychrosis viteana*, *Pectinophora gossypiella*, *Pieris rapae*, *Phyllonorycter* spp., *Leucoptera malifoliella*, *Phyllocnisitis citrella*

Coleoptera—*Diabrotica* spp., *Leptinotarsa decemlineata*, *Oulema oryzae*, *Anthonomus grandis*, *Lissorhoptrus oryzophilus*, *Agriotes* spp., *Melanotus communis*, *Popillia japonica*, *Cyclocephala* spp., *Tribolium* spp.

Homoptera—*Aphis* spp., *Myzus persicae*, *Rhopalosiphum* spp., *Dysaphis plantaginea*, *Toxoptera* spp., *Macrosiphum euphorbiae*, *Aulacorthum solani*, *Sitobion avenae*, *Metopolophium dirhodum*, *Schizaphis graminum*, *Brachycolus noxius*, *Nephotettix* spp., *Nilaparvata lugens*, *Sogatella furcifera*, *Laodelphax striatellus*, *Bemisia tabaci*, *Trialeurodes vaporariorum*, *Aleurodes proletella*, *Aleurothrixus floccosus*, *Quadraspidiotus perniciosus*, *Unaspis yanonensis*, *Ceroplastes rubens*, *Aonidiella aurantii*

Hemiptera—*Lygus* spp., *Eurygaster maura*, *Nezara viridula*, *Piezodorus guildingi*, *Leptocorisa varicornis*, *Cimex lectularius*, *Cimex hemipterus*

Thysanoptera—*Frankliniella* spp., *Thrips* spp., *Scirtothrips dorsalis*

Isoptera—*Reticulitermes flavipes*, *Coptotermes formosanus*, *Reticulitermes virginicus*, *Heterotermes aureus*, *Reticulitermes hesperus*, *Coptotermes frenchii*, *Shedorhinotermes* spp., *Reticulitermes santonensis*, *Reticulitermes grassei*, *Reticulitermes banyulensis*, *Reticulitermes speratus*, *Reticulitermes hageni*, *Reticulitermes tibialis*, *Zootermopsis* spp., *Incisitermes* spp., *Marginitermes* spp., *Macrotermes* spp., *Microcerotermes* spp., *Microtermes* spp.

Diptera—*Liriomyza* spp., *Musca domestica*, *Aedes* spp., *Culex* spp., *Anopheles* spp., *Fannia* spp., *Stomoxys* spp., Hymenoptera—*Iridomyrmex humilis*, *Solenopsis* spp., *Monomorium pharaonic*, *Atta* spp., *Pogonomyrmex* spp., *Camponotus* spp., *Monomorium* spp., *Tapinoma sessile*, *Tetramorium* spp., *Xylocapa* spp., *Vespula* spp., *Polistes* spp.

Mallophaga (chewing lice)

Anoplura (sucking lice)—*Pthirus pubis*, *Pediculus* spp.

Orthoptera (grasshoppers, crickets)—*Melanoplus* spp., *Locusta migratoria*, *Schistocerca gregaria*, *Gryllotalpidae* (mole crickets).

Blattoidea (cockroaches)—*Blatta orientalis*, *Blattella germanica*, *Periplaneta americana*, *Supella longipalpa*, *Periplaneta australasiae*, *Periplaneta brunnea*, *Parcoblatta pennsylvanica*, *Periplaneta fuliginosa*, *Pycnoscelus surinamensis*, Siphonaptera—*Ctenophalides* spp., *Pulex irritans*

Acari—*Tetranychus* spp., *Panonychus* spp., *Eotetranychus carpini*, *Phyllocoptruta oleivora*, *Aculus pelekassi*, *Brevipalpus phoenicis*, *Boophilus* spp., *Dermacentor variabilis*, *Rhipicephalus sanguineus*, *Amblyomma americanum*, *Ixodes* spp., *Notoedres cati*, *Sarcoptes scabiei*, *Dermatophagoides* spp.

Nematoda—*Dirofilaria immitis*, *Meloidogyne* spp., *Heterodera* spp., *Hoplolaimus columbus*, *Belonolaimus* spp., *Pratylenchus* spp., *Rotylenchus reniformis*, *Criconemella ornata*, *Ditylenchus* spp., *Aphelenchoides besseyi*, *Hirschmanniella* spp.

Compositions

The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by eight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsuiaied insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadillak; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methyl-chloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, niflluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, Coniothyrium minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmediphamethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

Before an insecticide can be used or sold commercially, such compound undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user and/or seller with product registration approval. Thereafter, in that locality where the product registration is granted and supported, such user and/or seller may use and/or sell such compound.

We claim:

1. A method of controlling insects which comprises applying to a locus where control is desired an insect-inactivating amount of the following compound

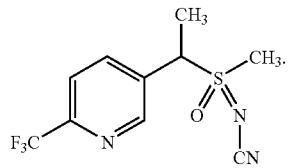

2. A method according to claim 1 wherein said locus has, or will have, one or more of the following therein, vegetable crops, fruit trees, nut trees, grape vines, ornamental plants, seeds, or grain.

3. A method according to claim 1 wherein said locus has, or will have, one or both of the following therein, rice or cotton.

4. A method according to claim 1 wherein said insects are one or more of the following, Lepidoptera, Coleoptera, Homoptera, Hemiptera, Thysanoptera, Isoptera, Diptera, Hymenoptera, Mallophaga, Anoplura, Orthoptera, Blattoidea, or Siphonaptera.

5. A method according to claim 1 wherein said insects are one or more of the following, cotton aphid, green peach aphid, brown planthopper, green planthopper, sweet potato white fly, or Eastern subterranean termite.

6. A method of inhibiting an insect, or other pests, which comprises applying to a locus an inhibiting amount of the following compound

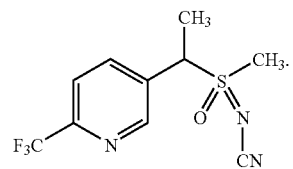

7. A method according to claim 6 wherein said locus has, or will have, one or more of the following therein, vegetable crops, fruit trees, nut trees, grape vines, ornamental plants, seeds, or grain.

8. A method according to claim 6 wherein said locus has, or will have, one or both of the following therein, rice or cotton.

9. A method according to claim 6 wherein said insects, or other pests, are one or more of the following, Lepidoptera, Coleoptera, Homoptera, Hemiptera, Thysanoptera, Isoptera, Diptera, Hymenoptera, Mallophaga, Anoplura, Orthoptera, Blattoidea, Siphonaptera, Acari, or Nematoda.

10. A method according to claim 6 wherein said insects are one or more of the following, cotton aphid, green peach aphid, brown planthopper, green planthopper, sweet potato white fly, Eastern subterranean termite, cat flea, or brown dog tick.

11. A method comprising applying to a domesticated animal the following compound

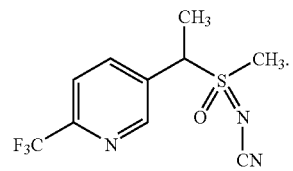

12. A method comprising applying to a seed the following compound

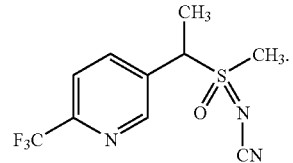

13. A method of controlling insects which comprises applying to a locus where control is desired a composition comprising:

(a) 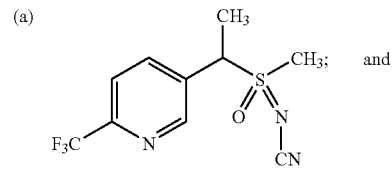 and (b) one or more compounds selected from antibiotic insecticides, macrocyclic lactone insecticides, avermectin insecticides, milbemycin insecticides, arsenical insecticides, biological insecticides, botanical insecticides, carbamate insecticides, benzofuranyl methylcarbamate insecticides, dimethylcarbamate insecticides, oxime carbamate insecticides, phenyl methylcarbamate insecticides, dinitrophenol insecticides, fluorine insecticides, formamidine insecticides, fumigant insecticides, inorganic insecticides, chitin synthesis inhibitors, juvenile hormone mimics, moulting hormone agonists, moulting hormones, moulting inhibitors, precocenes, nereistoxin analogue insecticides, nicotinoid insecticides, nitroguanidine insecticides, nitromethylene insecticides, pyridylmethylamine insecticides, organochlorine insecticides, cyclodiene insecticides, organophosphate insecticides, organothiophosphate insecticides, aliphatic organothiophosphate insecticides, aliphatic amide organothiophosphate insecticides, oxime organothiophosphate insecticides, heterocyclic organothiophosphate insecticides, benzothiopyran organothiophosphate insecticides, benzotriazine organothiophosphate insecticides, isoindole organothiophosphate insecticides, isoxazole organothiophosphate insecticides, pyrazolopyrimidine organothiophosphate insecticides, pyridine organothiophosphate insecticides, pyrimidine organothiophosphate insecticides, quinoxaline organothiophosphate insecticides, thiadiazole organothiophosphate insecticides, triazole organothiophosphate insecticides, phenyl organothiophosphate insecticides, phosphonate insecticides, phosphonothioate insecticides, phenyl ethylphosphonothioate insecticides, phenyl phenylphosphonothioate insecticides, phosphoramidate insecticides, phosphoramidothioate insecticides, phosphorodiamide insecticides, oxadiazine insecticides, phthalimide insecticides, pyrazole insecticides, pyrethroid ester insecticides, pyrethroid ether insecticides, pyrimidinamine insecticides, pyrrole insecticides, tetronic acid insecticides, thiourea insecticides, and urea insecticides.

14. A method of controlling insects which comprises applying to a locus where control is desired a composition comprising:

(a)

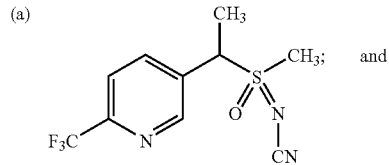

and (b) one or more compounds selected from allosamidin, thuringiensin, spinosad, spinetoram, abamectin, doramectin, emamectin, eprinomectin, ivermectin, selamectin, lepimectin, milbemectin, milbemycin oxime, moxidectin, calcium arsenate, copper acetoarsenite, copper arsenate, lead arsenate, potassium arsenite, sodium arsenite, anabasine, azadirachtin, d-limonene, nicotine, pyrethrins, cinerins, cinerin I, cinerin II, jasmolin I, jasmolin II, pyrethrin I, pyrethrin II, quassia, rotenone, ryania, sabadilla, bendiocarb, carbaryl, benfuracarb, carbofuran, carbosulfan, decarbofuran, furathiocarb, dimitan, dimetilan, hyquincarb, pirimicarb, alanycarb, aldicarb, aldoxycarb, butocarboxim, butoxycarboxim, methomyl, nitrilacarb, oxamyl, tazimcarb, thiocarboxime, thiodicarb, thiofanox, allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC, xylylcarb, dinex, dinoprop, dinosam, DNOC, barium hexafluorosilicate, cryolite, sodium fluoride, sodium hexafluorosilicate, sulfluramid, amitraz, chlordimeform, formetanate, formparanate, acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride, tetrachloroethane, borax, calcium polysulfide, copper oleate, mercurous chloride, potassium thiocyanate, sodium thiocyanate, bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron, epofenonane, fenoxycarb, hydroprene, kinoprene, methoprene, pyriproxyfen, triprene, juvenile hormone I, juvenile hormone II, juvenile hormone III, chromafenozide, halofenozide, methoxyfenozide, tebufenozide, α-ecdysone, ecdysterone, diofenolan, precocene I, precocene II, precocene III, dicyclanil, bensultap, cartap, thiocyclam, thiosultap, flonicamid, clothianidin, dinotefuran, imidacloprid, thiamethoxam, nitenpyram, nithiazine, acetamiprid, imidacloprid, nitenpyram, thiacloprid, bromo-DDT, camphechlor, DDT, pp'-DDT, ethyl-DDD, HCH, gamma-HCH, lindane, methoxychlor, pentachlorophenol, TDE, aldrin, bromocyclen, chlorbicyclen, chlordane, chlordecone, dieldrin, dilor, endosulfan, endrin, HEOD, heptachlor, HHDN, isobenzan, isodrin, kelevan, mirex, bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP, tetrachlorvinphos, dioxabenzofos, fosmethilan, phenthoate, acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos, thiometon, amidithion, cyanthoate, dimethoate, ethoate-methyl, formothion, mecarbam, omethoate, prothoate, sophamide, vamidothion, chlorphoxim, phoxim, phoxim-methyl, azamethiphos, coumaphos, coumithoate, dioxathion, endothion, menazon, morphothion, phosalone, pyraclofos, pyridaphenthion, quinothion, dithicrofos, thicrofos, azinphos-ethyl, azinphos-methyl, dialifos, phosmet, isoxathion, zolaprofos, chlorprazophos, pyrazophos, chlorpyrifos, chlorpyrifos-methyl, butathiofos, diazinon, etrimfos, lirimfos, pirimiphos-ethyl, pirimiphos-methyl, primidophos, pyrimitate, tebupirimfos, quinalphos, quinalphos-methyl, athidathion, lythidathion, methidathion, prothidathion, isazofos, triazophos, azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3, trifenofos, butonate, trichlorfon, mecarphon, fonofos, trichloronat, cyanofenphos, EPN, leptophos, crufomate, fenamiphos, fosthietan, mephosfolan, phosfolan, pirimetaphos, acephate, isocarbophos, isofenphos, methamidophos, propetamphos, dimefox, mazidox, mipafox, schradan, indoxacarb, dialifos, phosmet, tetramethrin, acetoprole, ethiprole, fipronil, pyrafluprole, pyriprole, tebufenpyrad, tolfenpyrad, vaniliprole, acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen, flufenerim, pyrimidifen, chlorfenapyr, spirodiclofen, spiromesifen, spirotetramat, diafenthiuron, flucofuron, sulcofuron, AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene, and triazamate.

15. A method of controlling insects which comprises applying to a locus where control is desired a composition comprising methoxyfenozide and

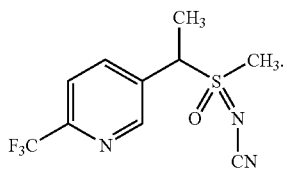

16. A method of controlling insects which comprises applying to a locus where control is desired a composition comprising spinosad and

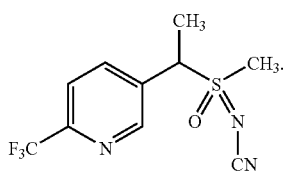

17. A method of controlling insects which comprises applying to a locus where control is desired a composition comprising spinetoram and

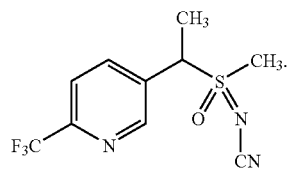

18. A method of controlling insects which comprises applying to a locus where control is desired a composition comprising:

(a) 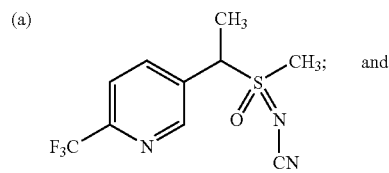 and (b) one or more of imidacloprid, acetamiprid, thiamethoxam, thiacloprid, dinotefuran, bifenthrin, and clothianidin.

19. A method of inhibiting an insect, or other pests, which comprises applying to a locus an inhibiting amount of a composition comprising:

(a) 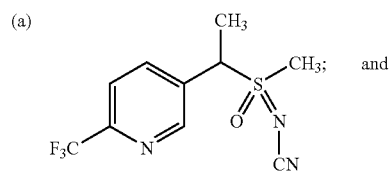 and (b) one or more compounds selected from antibiotic insecticides, macrocyclic lactone insecticides, avermectin insecticides, milbemycin insecticides, arsenical insecticides, biological insecticides, botanical insecticides, carbamate insecticides, benzofuranyl methylcarbamate insecticides, dimethylcarbamate insecticides, oxime carbamate insecticides, phenyl methylcarbamate insecticides, dinitrophenol insecticides, fluorine insecticides, formamidine insecticides, fumigant insecticides, inorganic insecticides, chitin synthesis inhibitors, juvenile hormone mimics, moulting hormone agonists, moulting hormones, moulting inhibitors, precocenes, nereistoxin analogue insecticides, nicotinoid insecticides, nitroguanidine insecticides, nitromethylene insecticides, pyridylmethylamine insecticides, organochlorine insecticides, cyclodiene insecticides, organophosphate insecticides, organothiophosphate insecticides, aliphatic organothiophosphate insecticides, aliphatic amide organothiophosphate insecticides, oxime organothiophosphate insecticides, heterocyclic organothiophosphate insecticides, benzothiopyran organothiophosphate insecticides, benzotriazine organothiophosphate insecticides, isoindole organothiophosphate insecticides, isoxazole organothiophosphate insecticides, pyrazolopyrimidine organothiophosphate insecticides, pyridine organothiophosphate insecticides, pyrimidine organothiophosphate insecticides, quinoxaline organothiophosphate insecticides, thiadiazole organothiophosphate insecticides, triazole organothiophosphate insecticides, phenyl organothiophosphate insecticides, phosphonate insecticides, phosphonothioate insecticides, phenyl ethylphosphonothioate insecticides, phenyl phenylphosphonothioate insecticides, phosphoramidate insecticides, phosphoramidothioate insecticides, phosphorodiamide insecticides, oxadiazine insecticides, phthalimide insecticides, pyrazole insecticides, pyrethroid ester insecticides, pyrethroid ether insecticides, pyrimidinamine insecticides, pyrrole insecticides, tetronic acid insecticides, thiourea insecticides, and urea insecticides.

20. A method of inhibiting an insect, or other pests, which comprises applying to a locus an inhibiting amount of a composition comprising:

(a) 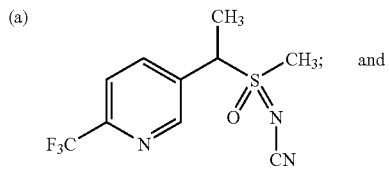

(b) one or more compounds selected from allosamidin, thuringiensin, spinosad, spinetoram, abamectin, doramectin, emamectin, eprinomectin, ivermectin, selamectin, lepimectin, milbemectin, milbemycin oxime, moxidectin, calcium arsenate, copper acetoarsenite, copper arsenate, lead arsenate, potassium arsenite, sodium arsenite, anabasine, azadirachtin, d-limonene, nicotine, pyrethrins, cinerins, cinerin I, cinerin II, jasmolin I, jasmolin II, pyrethrin I, pyrethrin II, quassia, rotenone, ryania, sabadilla, bendiocarb, carbaryl, benfuracarb, carbofuran, carbosulfan, decarbofuran, furathiocarb, dimitan, dimetilan, hyquincarb, pirimicarb, alanycarb, aldicarb, aldoxycarb, butocarboxim, butoxycarboxim, methomyl, nitrilacarb, oxamyl, tazimcarb, thiocarboxime, thiodicarb, thiofanox, allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC, xylylcarb, dinex, dinoprop, dinosam, DNOC, barium hexafluorosilicate, cryolite, sodium fluoride, sodium hexafluorosilicate, sulfluramid, amitraz, chlordimeform, formetanate, formparanate, acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride, tetrachloroethane, borax, calcium polysulfide, copper oleate, mercurous chloride, potassium thiocyanate, sodium thiocyanate, bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron, epofenonane, fenoxycarb, hydroprene, kinoprene, methoprene, pyriproxyfen, triprene, juvenile hormone I, juvenile hormone II, juvenile hormone III, chromafenozide, halofenozide, methoxyfenozide, tebufenozide, α-ecdysone, ecdysterone, diofenolan, precocene I, precocene II, precocene III, dicyclanil, bensultap, cartap, thiocyclam, thiosultap, flonicamid, clothianidin, dinotefuran, imidacloprid, thiamethoxam, nitenpyram, nithiazine, acetamiprid, imidacloprid, nitenpyram, thiacloprid, bromo-DDT, camphechlor, DDT, pp'-DDT, ethyl-DDD, HCH, gamma-HCH, lindane, methoxychlor, pentachlorophenol, TDE, aldrin, bromocyclen, chlorbicyclen, chlordane, chlordecone, dieldrin, dilor, endosulfan, endrin, HEOD, heptachlor, HHDN, isobenzan, isodrin, kelevan, mirex, bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP, tetrachlorvinphos, dioxabenzofos, fosmethilan, phenthoate, acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos, thiometon, amidithion, cyanthoate, dimethoate, ethoate-methyl, formothion, mecarbam, omethoate, prothoate, sophamide, vamidothion, chlorphoxim, phoxim, phoxim-methyl, azamethiphos, coumaphos, coumithoate, dioxathion, endothion, menazon, morphothion, phosalone, pyraclofos, pyridaphenthion, quinothion, dithicrofos, thicrofos, azinphos-ethyl, azinphos-methyl, dialifos, phosmet, isoxathion, zolaprofos, chlorprazophos, pyrazophos, chlorpyrifos, chlorpyrifos-methyl, butathiofos, diazinon, etrimfos, lirimfos, pirimiphos-ethyl, pirimiphos-methyl, primidophos, pyrimitate, tebupirimfos, quinalphos, quinalphos-methyl, athidathion, lythidathion, methidathion, prothidathion, isazofos, triazophos, azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3, trifenofos, butonate, trichlorfon, mecarphon, fonofos, trichloronat, cyanofenphos, EPN, leptophos, crufomate, fenamiphos, fosthietan, mephosfolan, phosfolan, pirimetaphos, acephate, isocarbophos, isofenphos, methamidophos, propetamphos, dimefox, mazidox, mipafox, schradan, indoxacarb, dialifos, phosmet, tetramethrin, acetoprole, ethiprole, fipronil, pyrafluprole, pyriprole, tebufenpyrad, tolfenpyrad, vaniliprole, acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen, flufenerim, pyrimidifen, chlorfenapyr, spirodiclofen, spiromesifen, spirotetramat, diafenthiuron, flucofuron, sulcofuron, AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene, and triazamate.

21. A method of inhibiting an insect, or other pests, which comprises applying to a locus an inhibiting amount of a composition comprising methoxyfenozide and

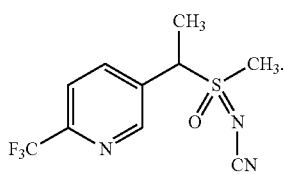

22. A method of inhibiting an insect, or other pests, which comprises applying to a locus an inhibiting amount of a composition comprising spinosad and

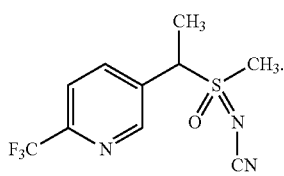

23. A method of inhibiting an insect, or other pests, which comprises applying to a locus an inhibiting amount of a composition comprising spinetoram and

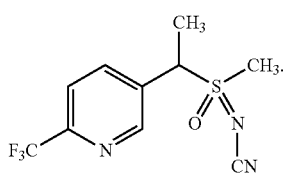

24. A method of inhibiting an insect, or other pests, which comprises applying to a locus an inhibiting amount of a composition comprising:

(a) 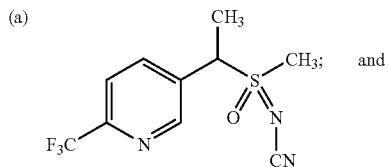 and (b) one or more of imidacloprid, acetamiprid, thiamethoxam, thiacloprid, dinotefuran, bifenthrin, and clothianidin.

25. A method comprising applying to a domesticated animal a composition comprising:

(a) 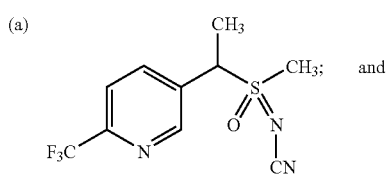 and (b) one or more compounds selected from antibiotic insecticides, macrocyclic lactone insecticides, avermectin insecticides, milbemycin insecticides, arsenical insecticides, biological insecticides, botanical insecticides, carbamate insecticides, benzofuranyl methylcarbamate insecticides, dimethylcarbamate insecticides, oxime carbamate insecticides, phenyl methylcarbamate insecticides, dinitrophenol insecticides, fluorine insecticides, formamidine insecticides, fumigant insecticides, inorganic insecticides, chitin synthesis inhibitors, juvenile hormone mimics, moulting hormone agonists, moulting hormones, moulting inhibitors, precocenes, nereistoxin analogue insecticides, nicotinoid insecticides, nitroguanidine insecticides, nitromethylene insecticides, pyridylmethylamine insecticides, organochlorine insecticides, cyclodiene insecticides, organophosphate insecticides, organothiophosphate insecticides, aliphatic organothiophosphate insecticides, aliphatic amide organothiophosphate insecticides, oxime organothiophosphate insecticides, heterocyclic organothiophosphate insecticides, benzothiopyran organothiophosphate insecticides, benzotriazine organothiophosphate insecticides, isoindole organothiophosphate insecticides, isoxazole organothiophosphate insecticides, pyrazolopyrimidine organothiophosphate insecticides, pyridine organothiophosphate insecticides, pyrimidine organothiophosphate insecticides, quinoxaline organothiophosphate insecticides, thiadiazole organothiophosphate insecticides, triazole organothiophosphate insecticides, phenyl organothiophosphate insecticides, phosphonate insecticides, phosphonothioate insecticides, phenyl ethylphosphonothioate insecticides, phenyl phenylphosphonothioate insecticides, phosphoramidate insecticides, phosphoramidothioate insecticides, phosphorodiamide insecticides, oxadiazine insecticides, phthalimide insecticides, pyrazole insecticides, pyrethroid ester insecticides, pyrethroid ether insecticides, pyrimidinamine insecticides, pyrrole insecticides, tetronic acid insecticides, thiourea insecticides, and urea insecticides.

26. A method comprising applying to a domesticated animal a composition comprising:

(a) 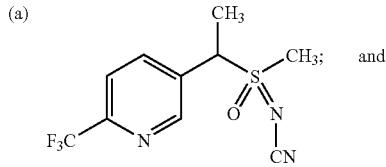 and (b) one or more compounds selected from allosamidin, thuringiensin, spinosad, spinetoram, abamectin, doramectin, emamectin, eprinomectin, ivermectin, selamectin, lepimectin, milbemectin, milbemycin oxime, moxidectin, calcium arsenate, copper acetoarsenite, copper arsenate, lead arsenate, potassium arsenite, sodium arsenite, anabasine, azadirachtin, d-limonene, nicotine, pyrethrins, cinerins, cinerin I, cinerin II, jasmolin I, jasmolin II, pyrethrin I, pyrethrin II, quassia, rotenone, ryania, sabadilla, bendiocarb, carbaryl, benfuracarb, carbofuran, carbosulfan, decarbofuran, furathiocarb, dimitan, dimetilan, hyquincarb, pirimicarb, alanycarb, aldicarb, aldoxycarb, butocarboxim, butoxycarboxim, methomyl, nitrilacarb, oxamyl, tazimcarb, thiocarboxime, thiodicarb, thiofanox, allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC, xylylcarb, dinex, dinoprop, dinosam, DNOC, barium hexafluorosilicate, cryolite, sodium fluoride, sodium hexafluorosilicate, sulfluramid, amitraz, chlordimeform, formetanate, formparanate, acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride, tetrachloroethane, borax, calcium polysulfide, copper oleate, mercurous chloride, potassium thiocyanate, sodium thiocyanate, bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron, epofenonane, fenoxycarb, hydroprene, kinoprene, methoprene, pyriproxyfen, triprene, juvenile hormone I, juvenile hormone II, juvenile hormone III, chromafenozide, halofenozide, methoxyfenozide, tebufenozide, α-ecdysone, ecdysterone, diofenolan, precocene I, precocene II, precocene III, dicyclanil, bensultap, cartap, thiocyclam, thiosultap, flonicamid, clothianidin, dinotefuran, imidacloprid, thiamethoxam, nitenpyram, nithiazine, acetamiprid, imidacloprid, nitenpyram, thiacloprid, bromo-DDT, camphechlor, DDT, pp'-DDT, ethyl-DDD, HCH, gamma-HCH, lindane, methoxychlor, pentachlorophenol, TDE, aldrin, bromocyclen, chlorbicyclen, chlordane, chlordecone, dieldrin, dilor, endosulfan, endrin, HEOD, heptachlor, HHDN, isobenzan, isodrin, kelevan, mirex, bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP, tetrachlorvinphos, dioxabenzofos, fosmethilan, phenthoate, acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos, thiometon, amidithion, cyanthoate, dimethoate, ethoate-methyl, formothion, mecarbam, omethoate, prothoate, sophamide, vamidothion, chlorphoxim, phoxim, phoxim-methyl, azamethiphos, coumaphos, coumithoate, dioxathion, endothion, menazon, morphothion, phosalone, pyraclofos, pyridaphenthion, quinothion, dithicrofos, thicrofos, azinphos-ethyl, azinphos-methyl, dialifos, phosmet, isoxathion, zolaprofos, chlorprazophos, pyrazophos, chlorpyrifos, chlorpyrifos-methyl, butathiofos, diazinon, etrimfos, lirimfos, pirimiphos-ethyl, pirimiphos-methyl, primidophos, pyrimitate, tebupirimfos, quinalphos, quinalphos-methyl, athidathion, lythidathion, methidathion, prothidathion, isazofos, triazophos, azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3, trifenofos, butonate, trichlorfon, mecarphon, fonofos, trichloronat, cyanofenphos, EPN, leptophos, crufomate, fenamiphos, fosthietan, mephosfolan, phosfolan, pirimetaphos, acephate, isocarbophos, isofenphos, methamidophos, propetamphos, dimefox, mazidox, mipafox, schradan, indoxacarb, dialifos, phosmet, tetramethrin, acetoprole, ethiprole, fipronil, pyrafluprole, pyriprole, tebufenpyrad, tolfenpyrad, vaniliprole, acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen, flufenerim, pyrimidifen, chlorfenapyr, spirodiclofen, spiromesifen, spirotetramat, diafenthiuron, flucofuron, sulcofuron, AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene, and triazamate.

27. A method comprising applying to a domesticated animal a composition comprising methoxyfenozide and

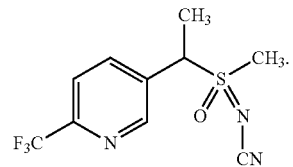

28. A method comprising applying to a domesticated animal a composition comprising spinosad and

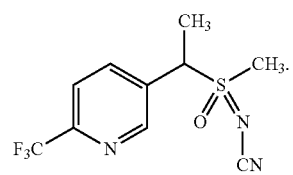

29. A method comprising applying to a domesticated animal a composition comprising spinetoram and

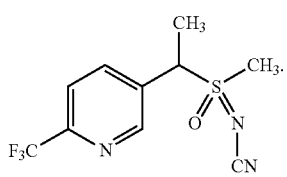

30. A method comprising applying to a domesticated animal a composition comprising:

(a) 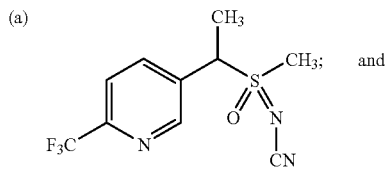 and (b) one or more of imidacloprid, acetamiprid, thiamethoxam, thiacloprid, dinotefuran, bifenthrin, and clothianidin.

31. A method comprising applying to a seed a composition comprising:

(a) 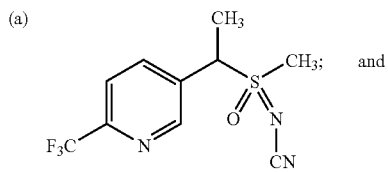 and (b) one or more compounds selected from antibiotic insecticides, macrocyclic lactone insecticides, avermectin insecticides, milbemycin insecticides, arsenical insecticides, biological insecticides, botanical insecticides, carbamate insecticides, benzofuranyl methylcarbamate insecticides, dimethylcarbamate insecticides, oxime carbamate insecticides, phenyl methylcarbamate insecticides, dinitrophenol insecticides, fluorine insecticides, formamidine insecticides, fumigant insecticides, inorganic insecticides, chitin synthesis inhibitors, juvenile hormone mimics, moulting hormone agonists, moulting hormones, moulting inhibitors, precocenes, nereistoxin analogue insecticides, nicotinoid insecticides, nitroguanidine insecticides, nitromethylene insecticides, pyridylmethylamine insecticides, organochlorine insecticides, cyclodiene insecticides, organophosphate insecticides, organothiophosphate insecticides, aliphatic organothiophosphate insecticides, aliphatic amide organothiophosphate insecticides, oxime organothiophosphate insecticides, heterocyclic organothiophosphate insecticides, benzothiopyran organothiophosphate insecticides, benzotriazine organothiophosphate insecticides, isoindole organothiophosphate insecticides, isoxazole organothiophosphate insecticides, pyrazolopyrimidine organothiophosphate insecticides, pyridine organothiophosphate insecticides, pyrimidine organothiophosphate insecticides, quinoxaline organothiophosphate insecticides, thiadiazole organothiophosphate insecticides, triazole organothiophosphate insecticides, phenyl organothiophosphate insecticides, phosphonate insecticides, phosphonothioate insecticides, phenyl ethylphosphonothioate insecticides, phenyl phenylphosphonothioate insecticides, phosphoramidate insecticides, phosphoramidothioate insecticides, phosphorodiamide insecticides, oxadiazine insecticides, phthalimide insecticides, pyrazole insecticides, pyrethroid ester insecticides, pyrethroid ether insecticides, pyrimidinamine insecticides, pyrrole insecticides, tetronic acid insecticides, thiourea insecticides, and urea insecticides.

32. A method comprising applying to a seed a composition comprising:

(a) 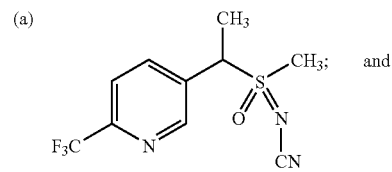 and (b) one or more compounds selected from allosamidin, thuringiensin, spinosad, spinetoram, abamectin, doramectin, emamectin, eprinomectin, ivermectin, selamectin, lepimectin, milbemectin, milbemycin oxime, moxidectin, calcium arsenate, copper acetoarsenite, copper arsenate, lead arsenate, potassium arsenite, sodium arsenite, anabasine, azadirachtin, d-limonene, nicotine, pyrethrins, cinerins, cinerin I, cinerin II, jasmolin I, jasmolin II, pyrethrin I, pyrethrin II, quassia, rotenone, ryania, sabadilla, bendiocarb, carbaryl, benfuracarb, carbofuran, carbosulfan, decarbofuran, furathiocarb, dimitan, dimetilan, hyquincarb, pirimicarb, alanycarb, aldicarb, aldoxycarb, butocarboxim, butoxycarboxim, methomyl, nitrilacarb, oxamyl, tazimcarb, thiocarboxime, thiodicarb, thiofanox, allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC, xylylcarb, dinex, dinoprop, dinosam, DNOC, barium hexafluorosilicate, cryolite, sodium fluoride, sodium hexafluorosilicate, sulfluramid, amitraz, chlordimeform, formetanate, formparanate, acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride, tetrachloroethane, borax, calcium polysulfide, copper oleate, mercurous chloride, potassium thiocyanate, sodium thiocyanate, bistrifluron, buprofezin, chlorfluazuron, cyromazine, diflubenzuron, flucycloxuron, flufenoxuron, hexaflumuron, lufenuron, novaluron, noviflumuron, penfluron, teflubenzuron, triflumuron, epofenonane, fenoxycarb, hydroprene, kinoprene, methoprene, pyriproxyfen, triprene, juvenile hormone I, juvenile hormone II, juvenile hormone III, chromafenozide, halofenozide, methoxyfenozide, tebufenozide, α-ecdysone, ecdysterone, diofenolan, precocene I, precocene II, precocene III, dicyclanil, bensultap, cartap, thiocyclam, thiosultap, flonicamid, clothianidin, dinotefuran, imidacloprid, thiamethoxam, nitenpyram, nithiazine, acetamiprid, imidacloprid, nitenpyram, thiacloprid, bromo-DDT, camphechlor, DDT, pp'-DDT, ethyl-DDD, HCH, gamma-HCH, lindane, methoxychlor, pentachlorophenol, TDE, aldrin, bromocyclen, chlorbicyclen, chlordane, chlordecone, dieldrin, dilor, endosulfan, endrin, HEOD, heptachlor, HHDN, isobenzan, isodrin, kelevan, mirex, bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP, tetrachlorvinphos, dioxabenzofos, fosmethilan, phenthoate, acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos, thiometon, amidithion, cyanthoate, dimethoate, ethoate-methyl, formothion, mecarbam, omethoate, prothoate, sophamide, vamidothion, chlorphoxim, phoxim, phoxim-methyl, azamethiphos, coumaphos, coumithoate, dioxathion, endothion, menazon, morphothion, phosalone, pyraclofos, pyridaphenthion, quinothion, dithicrofos, thicrofos, azinphos-ethyl, azinphos-methyl, dialifos, phosmet, isoxathion, zolaprofos, chlorprazophos, pyrazophos, chlorpyrifos, chlorpyrifos-methyl, butathiofos, diazinon, etrimfos, lirimfos, pirimiphos-ethyl, pirimiphos-methyl, primidophos, pyrimitate, tebupirimfos, quinalphos, quinalphos-methyl, athidathion, lythidathion, methidathion, prothidathion, isazofos, triazophos, azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3, trifenofos, butonate, trichlorfon, mecarphon, fonofos, trichloronat, cyanofenphos, EPN, leptophos, crufomate, fenamiphos, fosthietan, mephosfolan, phosfolan, pirimetaphos, acephate, isocarbophos, isofenphos, methamidophos, propetamphos, dimefox, mazidox, mipafox, schradan, indoxacarb, dialifos, phosmet, tetramethrin, acetoprole, ethiprole, fipronil, pyrafluprole, pyriprole, tebufenpyrad, tolfenpyrad, vaniliprole, acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute, silafluofen, flufenerim, pyrimidifen, chlorfenapyr, spirodiclofen, spiromesifen, spirotetramat, diafenthiuron, flucofuron, sulcofuron, AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene, and triazamate.

33. A method comprising applying to a seed a composition comprising methoxyfenozide and

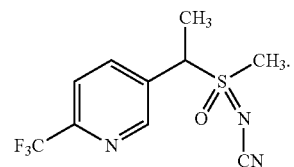

34. A method comprising applying to a seed a composition comprising spinosad and

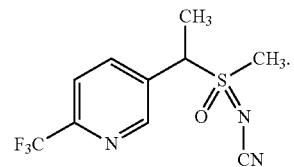

35. A method comprising applying to a seed a composition comprising spinetoram and

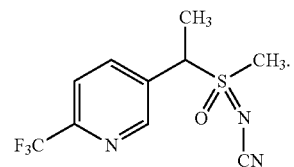

36. A method comprising applying to a seed a composition comprising:

(a) 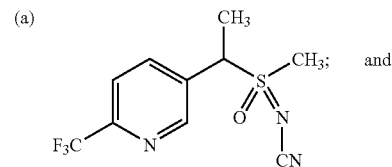 and (b) one or more of imidacloprid, acetamiprid, thiamethoxam, thiacloprid, dinotefuran, bifenthrin, and clothianidin.

37. A method according to one of claims 13-18 wherein said locus has, or will have, one or more of the following therein, vegetable crops, fruit trees, nut trees, grape vines, ornamental plants, seeds, or grain.

38. A method according to one of claims 13-18 wherein said locus has, or will have, one or both of the following therein, rice or cotton.

39. A method according to one of claims 13-18 wherein said insects are one or more of the following, Lepidoptera, Coleoptera, Homoptera, Hemiptera, Thysanoptera, Isoptera, Diptera, Hymenoptera, Mallophaga, Anoplura, Orthoptera, Blattoidea, or Siphonaptera.

40. A method according to one of claims 13-18 wherein said insects are one or more of the following, cotton aphid, green peach aphid, brown planthopper, green planthopper, sweet potato white fly, or Eastern subterranean termite.

41. A method according to one of claims 19-24 wherein said locus has, or will have, one or more of the following therein, vegetable crops, fruit trees, nut trees, grape vines, ornamental plants, seeds, or grain.

42. A method according to one of claims 19-24 wherein said locus has, or will have, one or both of the following therein, rice or cotton.

43. A method according to one of claims 19-24 wherein said insects, or other pests, are one or more of the following, Lepidoptera, Coleoptera, Homoptera, Hemiptera, Thysanoptera, Isoptera, Diptera, Hymenoptera, Mallophaga, Anoplura, Orthoptera, Blattoidea, Siphonaptera, Acari, or Nematoda.

44. A method according to one of claims 19-24 wherein said insects are one or more of the following, cotton aphid, green peach aphid, brown planthopper, green planthopper, sweet potato white fly, Eastern subterranean termite, cat flea, or brown dog tick.

* * * * *